(12) United States Patent
Greene et al.

(10) Patent No.: US 9,701,631 B2
(45) Date of Patent: Jul. 11, 2017

(54) TIP60 INHIBITORS

(75) Inventors: Mark I. Greene, Penn Valley, PA (US);
Alan Berezov, West Hollywood, CA (US); Yan Xiao, Philadelphia, PA (US); Hongtao Zhang, Paoli, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 67 days.

(21) Appl. No.: 13/991,192

(22) PCT Filed: Dec. 2, 2011

(86) PCT No.: PCT/US2011/063043
§ 371 (c)(1),
(2), (4) Date: Dec. 18, 2013

(87) PCT Pub. No.: WO2012/075380
PCT Pub. Date: Jun. 7, 2012

(65) Prior Publication Data
US 2014/0187579 A1 Jul. 3, 2014

Related U.S. Application Data

(60) Provisional application No. 61/419,465, filed on Dec. 3, 2010, provisional application No. 61/419,473, filed on Dec. 3, 2010.

(51) Int. Cl.
| | | |
|---|---|---|
| *C07D 401/00* | (2006.01) |
| *C07D 215/04* | (2006.01) |
| *C07D 295/00* | (2006.01) |
| *C07D 207/277* | (2006.01) |
| *A61K 31/4015* | (2006.01) |
| *A61K 31/4709* | (2006.01) |
| *C07D 401/12* | (2006.01) |

(52) U.S. Cl.
CPC ...... *C07D 207/277* (2013.01); *A61K 31/4015* (2013.01); *A61K 31/4709* (2013.01); *C07D 401/12* (2013.01)

(58) Field of Classification Search
USPC ............ 548/543, 547; 546/135, 181, 279, 1; 514/408
See application file for complete search history.

(56) References Cited

U.S. PATENT DOCUMENTS

| 7,067,549 B2 | 6/2006 | Isler et al. |
| 8,497,285 B2 | 7/2013 | Greene et al. |
| 2005/0192292 A1 | 9/2005 | Isler et al. |
| 2005/0261290 A1 | 11/2005 | Cheng et al. |
| 2010/0061984 A1 | 3/2010 | Greene et al. |

FOREIGN PATENT DOCUMENTS

| GB | WO 0139877 A1 * | 6/2001 | ............... B01J 4/02 |
| WO | WO 0139877 A1 * | 6/2001 | |
| WO | WO 2007/084775 | 7/2007 | |
| WO | WO 2012/075380 A1 | 6/2012 | |

OTHER PUBLICATIONS

McKim, A.S. et al., (PharmTechTalk, published May 2, 2008).*
Enamine HTS Library Product Page for compound Z30874011. Published Jul. 13, 2004.*
Maybridge PLC HTS Library Product Page for compound HTS 109005, HTS10906, HTS10908 and HTS10909. CAS Registry Index of Jun. 30, 2004.*
Remington: The Science and Practice of Pharmacy 21$^{st}$ Edition. pp. 89, pp. 720-722. Published 2005.*
Waybright, T.J., et al., Journal of Biomedical Screening vol. 14 pp. 708-715. Published 2009.*
Maybridge PLC HTS Library Product Page for compounds HTS 10905, HTS10906, HTS10908 and HTS 10909 with CAS Registry Index of Jun. 30, 2004.*
Ito, N., et al., Cancer Sci. vol. 94, pp. 3-8. Published 2003.*
Waybright, T.J., et al., (Journal of Biomolecular Screening vol. 14, pp. 708-715 published 2009).*
Ito, N., et al., (Cancer Sci. vol. 94, pp. 3-8. Published 2003).*
Waybright, T.J., et al., (Journal of Biomolecular Screening vol. 14, pp. 708-715. Published 2009).*
Maybridge PLC HTS Library Product Page for HTS 10905, 10906, 10908 and 10909 with CAS Registry Index of Jun. 30, 2004.*
Akimova et al, "Histone/Protein Deacetylase Inhibitors increase suppressive functions of human FOXP3+ Tregs," Clin. Immunol., Sep. 2010, 136(3), 348-363.
Fingl et al, "The Pharmacological Basis of Therapeutics", 1975, Ch.1, p. 1.
Finnin, B., and Morgan, T., "Transdermal Penetration Enhancers: Applications, Limitations, and Potential", Journal of Pharmaceutical Sciences, Oct. 1999, 88(10), 955-958.
Li et al, "FOXP3 Interactions With Histone Acetyltransferase and Class Ii Histone Deacetylases are Required for Repression", PNAS, Mar. 13, 2007, 104(11), 4571-4576.
Sugden, J.K. et al. "Some Pyrrolidine Derivatives as Antispasmodics", J. Med. Chem. 14(1), 1971, pp. 76-78.
Tao et al, "Deacetylase Inhibition Promotes The Generation and Function of Regulatory T Cells", Nature Medicine, Nov. 2007, 13(11), 1299-307.
Tao et al, "Regulatory T Cell Expression of Herpesvirus Entry Mediator Suppresses the Function of B and T Lymphocyte Attenuator-Positive Effector T Cells1", Journal of Immunology, 2008, 180: 6649-6655.
Tao, R. and Hancock, W., "Resistance of Foxp3+ Regulatory T Cells to Nur77-Induced Apoptosis Promotes Allograft Survival", May 2008, 3(5), e2321.

* cited by examiner

*Primary Examiner* — Timothy Thomas
*Assistant Examiner* — George W Kosturko
(74) *Attorney, Agent, or Firm* — Baker & Hostetler LLP

(57) ABSTRACT

This invention is in the fields of immunology and autoimmunity. More particularly it concerns pharmaceutical compositions comprising compounds which are useful agents for inhibiting the functions of TIP60 and the use of such compounds in the treatment of an individual suffering, for example, from ulcerative colitis and other irritable bowel diseases.

25 Claims, 20 Drawing Sheets

B7-500x

Treg : Teff ratio =     0:1                                    0.125:1

Treg : Teff ratio =    0.25:1              0.5:1                    1:1

B7-A-500x

Treg : Teff ratio =        0:1                            0.125:1

Treg : Teff ratio =    0.25:1              0.5:1                      1:1

B7-B-500x

Treg : Teff ratio =    0:1                    0.125:1

Treg : Teff ratio =    0.25:1         0.5:1            1:1

B7-C-500x

Treg : Teff ratio =    0:1    0.125:1

Treg : Teff ratio =    0.25:1    0.5:1    1:1

FIGURE 12A. *Colitis 1* – TIP60dn mice are resistant to DSS colitis
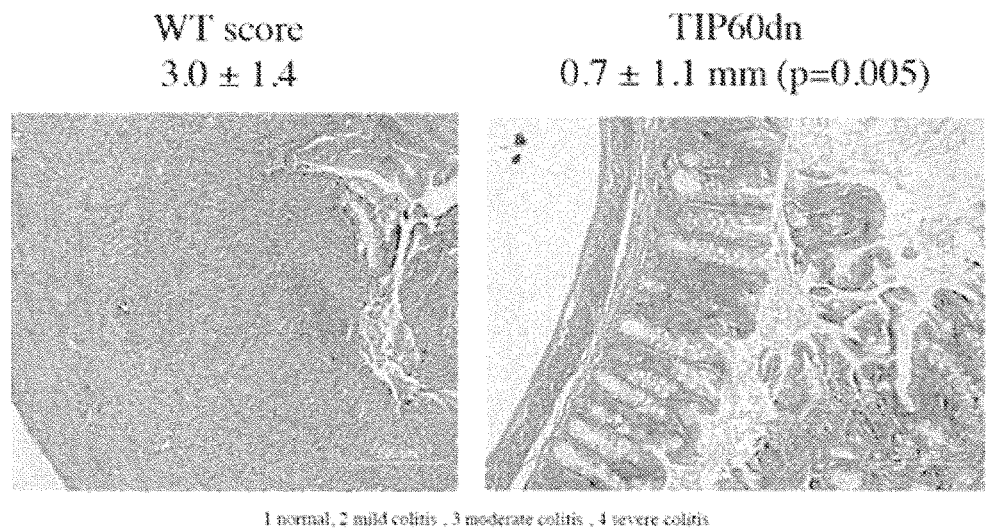
1 normal, 2 mild colitis, 3 moderate colitis, 4 severe colitis
FIGURE 12B. *Colitis 2* – TIP60dn are more effective than WT Tregs in suppressing adoptively transferred colitis
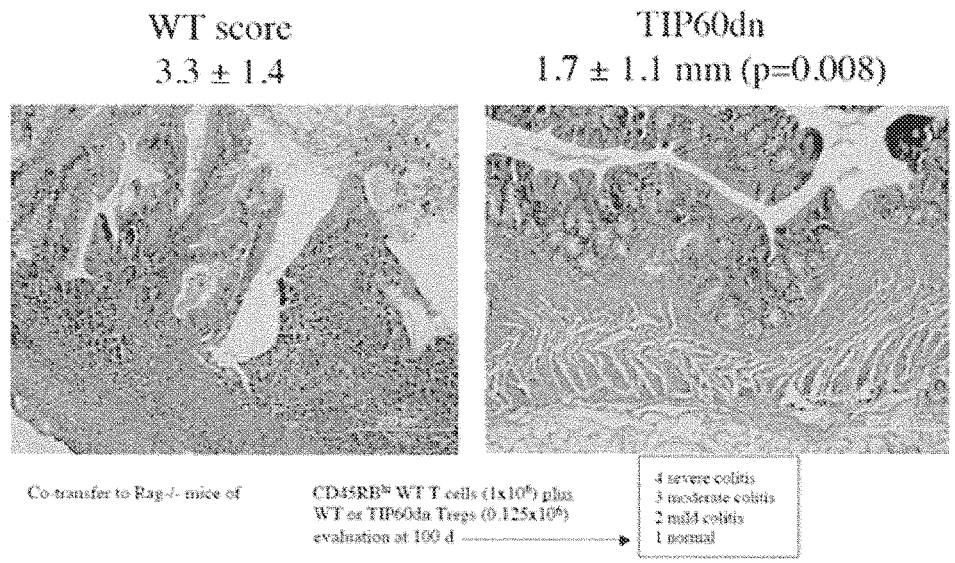

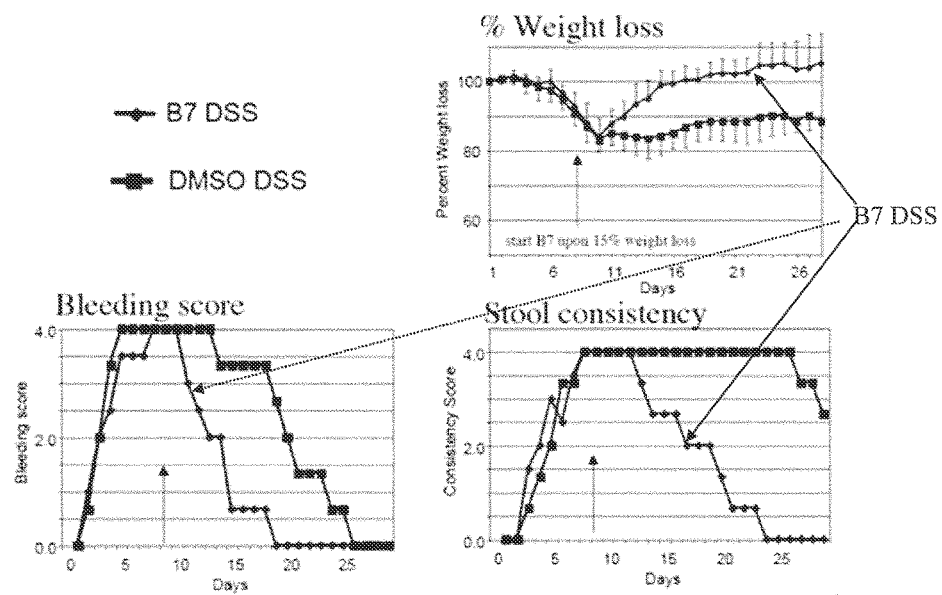
FIGURE 12C. *Colitis 3* – *TIP60i-treated mice are resistant to DSS colitis*

TIP60 INHIBITORS

CROSS-REFERENCE TO RELATED APPLICATIONS

This application is the National Stage of International Application No. PCT/US2011/063043, filed Dec. 2, 2011, which claims the benefit of U.S. Provisional Application No. 61/419,465 filed Dec. 3, 2010, and U.S. Provisional Application No. 61/419,473, filed Dec. 3, 2010, the disclosures of which are incorporated herein by reference in their entireties.

GOVERNMENT RIGHTS

This invention was made with government support under grant AI073489 awarded by the National Institutes of Health. The government has certain rights in the invention.

TECHNICAL FIELD

This invention is in the fields of immunology and autoimmunity. More particularly it concerns pharmaceutical compositions comprising compounds which are useful agents for inhibiting the functions of TIP60 and in the treatment of an individual suffering, for example, from ulcerative colitis and other irritable bowel diseases.

BACKGROUND

The incidence of inflammatory bowel disease (IBD), including Crohn's disease and ulcerative colitis, is currently between 75-150 cases per 100,000 individuals in the US and increasing. The development of IBD is influenced by an individual's genetic background, immune responses and environment (including gut microbiota and toxin exposure). Clinical and experimental data indicate that the development of IBD is mediated primarily by CD4+ T cells. Current best practice therapy for IBD involves cytokine targeting using biologic therapies up to and including parental administration of anti-TNF-α biologics. However, such treatments protocols are expensive to produce and deliver, and are prone to induce blocking antibodies that can limit their long-term safety and efficacy.

Clinicians believe that, despite the availability of anti-TNF-α biologics for the treatment of moderate to severe Crohn's disease and ulcerative colitis, there is a major unmet need for drugs that induce and maintain remission without immune suppression and the need for corticosteroids.

Given continuous exposure of the gut to microbial and other antigens, the regulation of host inflammatory responses by thymic-derived FOXP3+ T regulatory (Treg) cells is crucial to the maintenance of health. Both humans and mice with defects in FOXP3 develop severe autoimmunity, including colitis, and adoptive transfer of Tregs can reverse established colitis in murine models, though this is not practical for long-term clinical therapy. By contrast, identifying ways to pharmacologically promote Treg suppressive functions has considerable potential for therapeutic application in patients with IBD.

Previous research has shown that FOXP3 acetylation and Tregs functions are controlled by the interactions of histone/protein acetyltransferases (HATs) and histone/protein deacetylases (HDACs). See, for example, Li et al., "FOXP interactions with histone acetyltransferase and class II histone deacetylases are required for suppression," Proc. Natl. acad. Sci. USA, 2007 Mar. 13: 104 (11): 4571-6, which is incorporated by reference herein. Specifically, the HAT enzyme, TIP60, recruits p300 to a FOXP3 complex and p300-mediated acetylation of FOXP3 is required for optimal Treg functions, whereas autoacetylation of TIP60 promotes disassembly of this activating complex (see, e.g., FIG. 6).

Increased FOXP3 acetylation can be achieved by use of histone/protein deacetylase (HDAC) inhibitors, as would be relevant to autoimmunity and transplant rejection, whereas decreased FOXP3 acetylation can be achieved using histone/protein acetyltransferase (HAT) inhibitors, as might be useful in various malignancies wherein the Treg population may limit host anti-tumor responses. TIP60 inhibitors play a special role in promoting FOXP3 acetylation by prolonging the recruitment of p300 to the FOXP3 signaling complex.

Additional information on this subject is available in a co-pending application, U.S. patent application Ser. No. 12/161,192, published as U.S. Patent Application Publication US 2010/0061984, which is a U.S. National Phase Application of PCT/US2007/001677, "Compositions and Methods for Modulation of Suppressor T Cell Activation," which is incorporated by references for all purposes herein.

SUMMARY

Importantly, the present invention describes small molecules that achieve the same goal, namely inhibition of TIP60's active site while maintaining its scaffolding ability. As a result, TIP60 binds to FOXP3 and recruits p300 but auto-acetylation and subsequent dissociation of the complex is markedly decreased, leading to increased overall FOXP3 acetylation and Treg suppressive functions.

One embodiment of this invention is a pharmaceutical composition comprising an effective amount of a compound having a structure of Formula 1:

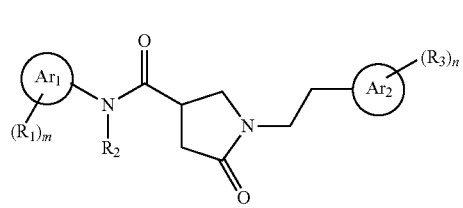

(I)

wherein $Ar_1$ and $Ar_2$ are each independently $C_6$-$C_{10}$ aryl or $C_3$-$C_{10}$ heteroaryl;
$R_1$ and $R_3$ are each independently at each occurrence alkyl, halo, hydroxyl, cyano, nitro, or alkoxy;
$R_2$ is H or alkyl; and
m and n are independently 0, 1, or 2;
and at least one pharmaceutically acceptable carrier, diluent, excipient or auxiliary.

More specific embodiments include those wherein the compositions comprise compounds having a structure according to B7, B7A, B7B, B7C, or B7G:

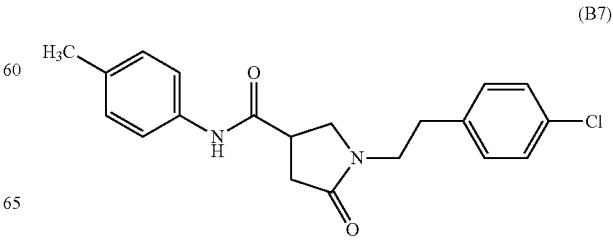

(B7)

-continued

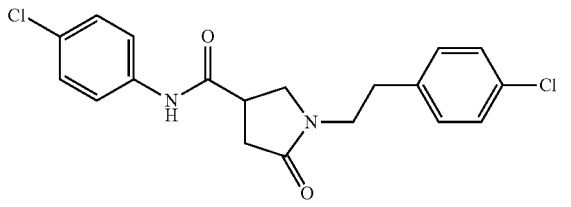
(B7A)

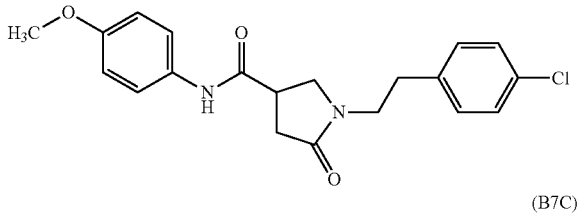
(B7B)

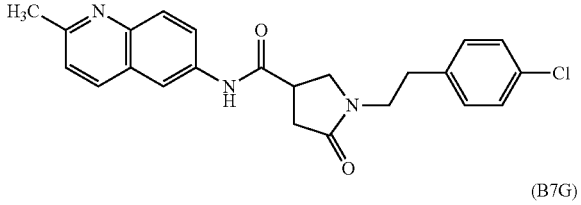
(B7C)

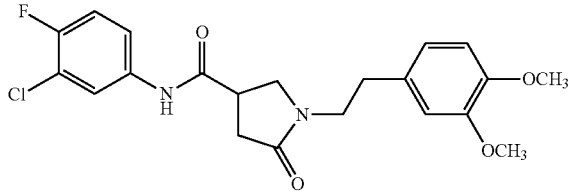
(B7G)

Other embodiments include those wherein said compositions inhibits histone acetyltransferase (HAT) activity or expression. Still other embodiments include those wherein said compositions that inhibits HAT activity or expression contain a compound that inhibits TIP60 activity or expression.

In certain embodiments, the compositions are separately adapted for oral, parenteral (including intratumor, intravenous, subcutaneous, intraperitoneal, or intramuscular administration), nasal, intrabronchial, or topical administration.

BRIEF DESCRIPTION OF THE DRAWINGS

FIG. 8A are the data for DMSO without B7; FIG. 8B are the data for B7-1000×; FIG. 8C are the data for B7-4000×; and FIG. 8D are the data for B7-8000. In each case, the 1000×/4000×/8000× refers to the dilution factor of the B7, from an original 10 mM solution of B7; e.g., 1000× represents a solution diluted by a factor of 1000, so as to result in a 10 micromolar solution. The numbers in the upper left corner of the plot (e.g., 88, 81, 74, 65, and 37 of FIG. 8A) refer to the measured percentage of proliferated cells.

FIG. 10A are the data for DMSO without any B7-type inhibitor; FIG. 10B are the data for B7-500×; FIG. 10C are the data for B7A-500×; FIG. 10D are the data for B7B-500; and FIG. 10E are the data for B7C-500×. In each case, the 500× refers to the dilution factor of the B7/B7A/B7B/B7C, from an original 10 mM solution of the compound; e.g., 500× represents a solution diluted by a factor of 500, so as to result in a 20 micromolar solution.

FIGS. 12A-C are the result of experiments described in Example 5. In particular, FIG. 12A shows colon tissue sections of mice taken 3 weeks after the mice were exposed to 5 days of dextrane sodium sulfite irritants. FIG. 12B shows colon tissue sections of mice after the adoptive transfer experiments of Example 4. FIG. 12C provide graphical data for weight loss, bleeding score, and stool consistency (i.e., higher score reflects higher levels of diarrhea), wherein the mice were first subjected to DSS irritation, then subset populations were remedially treated after 8 days with the compound having Structure B7.

DETAILED DESCRIPTION OF ILLUSTRATIVE EMBODIMENTS

Figure 1:
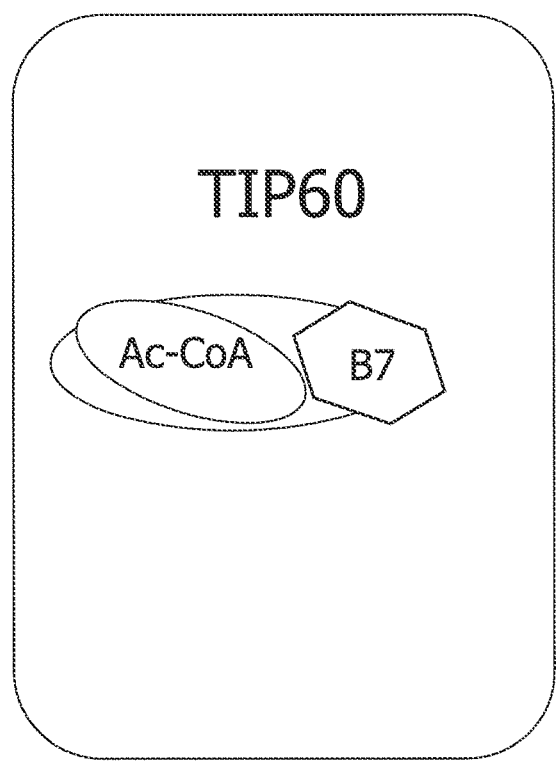
FIG. 1. is a cartoon representation of the mode of interaction between the target inhibitor B7 and TIP60-Acetyl-CoA complex, wherein the B7 is believed to inhibit TIP60 non-competitively by forming a functionally impaired complex with TIP60 and Acetyl-CoA.
Figure 2:
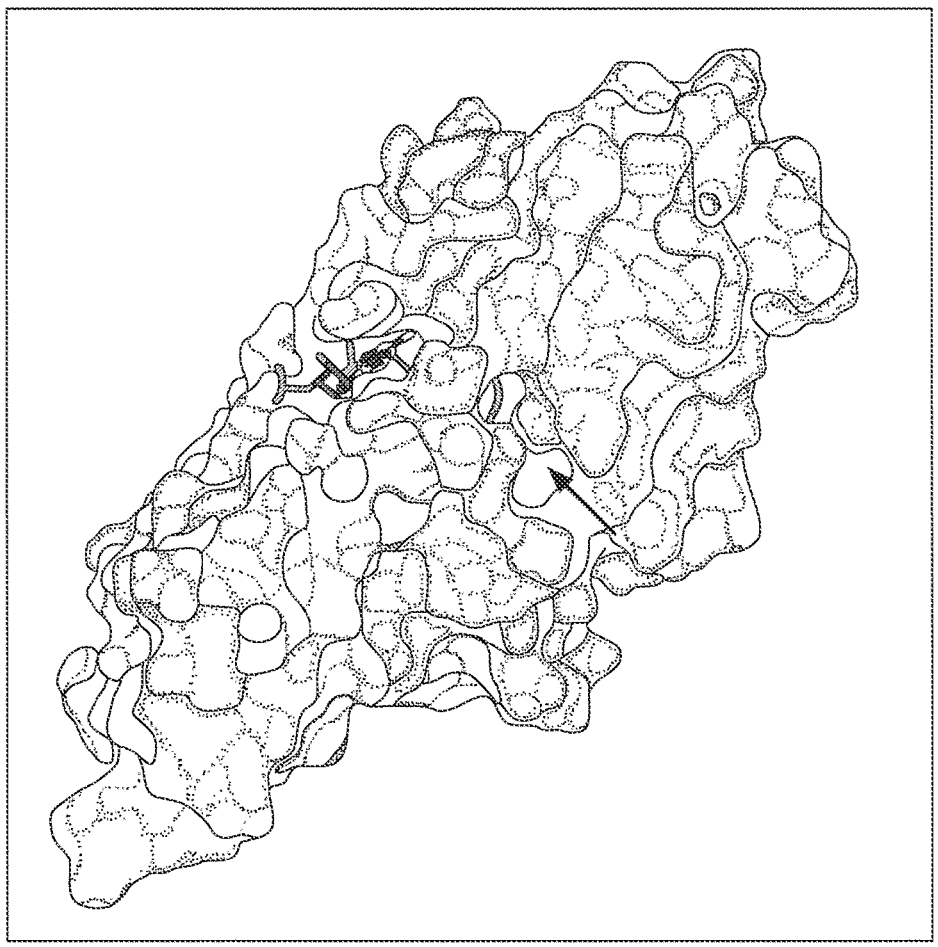
FIG. 2. is a representation of the crystal structure of TIP60-Acetyl-CoA complex, where the arrow points to cavity believed where the inhibitors interact.
Figure 3:
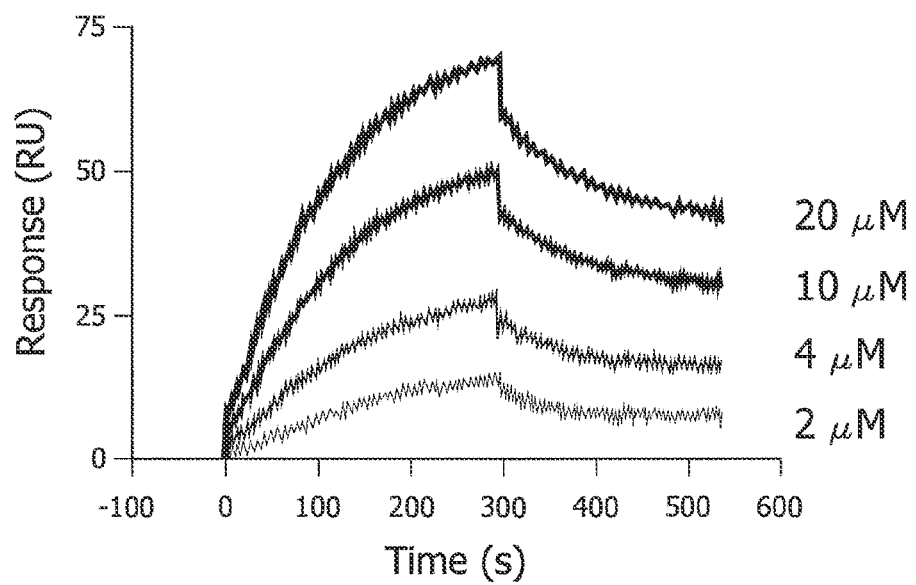
FIG. 3. is graphical representation of FOXP3-TIP60 interaction studied by means of Surface Plasmon Resonance (SPR) spectroscopy. The N-terminal fragment of FOXP3 was tested for binding to TIP60 in a range of concentrations from 2 to 20 uM. The obtained dose response curves are shown in FIG. 3. Curve fitting to a 1:1 binding model was used to estimate the association ($k_{on}$) and dissociation ($k_{off}$) rate constants. The dissociated constant of about 5 uM was then calculated as a $k_{off}/k_{on}$ ratio.

The present invention may be understood more readily by reference to the following detailed description taken in connection with the accompanying Figures and Examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the compounds and to the resulting pharmaceutical compositions and methods of manufacture and use.

Importantly, the present invention describes pharmaceutical compositions containing at least one small molecule that achieve the same goal, namely inhibition of TIP60's active site while maintaining its scaffolding ability. As a result, TIP60 binds to FOXP3 and recruits p300 but autoacetylation and subsequent dissociation of the complex is markedly decreased, leading to increased overall FOXP3 acetylation and Treg suppressive functions.

The present invention relates to compounds and pharmaceutical compositions useful for inhibiting the functions of TIP60 and to methods of using such compounds and compositions in the treatment of an individual suffering, for example, from ulcerative colitis and other irritable bowel diseases.

The invention teaches pharmaceutical compositions comprising compounds having the general structure of Formula I:

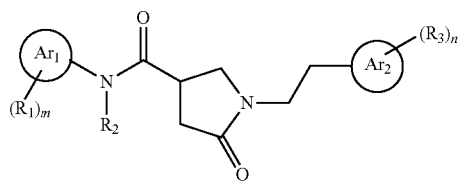

(I)

wherein $Ar_1$ and $Ar_2$ are each independently $C_6$-$C_{10}$ aryl or $C_3$-$C_{10}$ heteroaryl;
$R_1$ and $R_3$ are each independently at each occurrence alkyl, halo, hydroxyl, cyano, nitro, or alkoxy;
$R_2$ is H or alkyl; and
m and n are independently 0, 1, 2, or 3.

As used herein, the terms "aryl" refers to a carbocyclic (all carbon) ring that has a fully delocalized pi-electron system. The "aryl" group can be made up of two or more fused rings (rings that share two adjacent carbon atoms). When the aryl is a fused ring system, then the ring that is connected to the rest of the molecule has a fully delocalized pi-electron system. The other ring(s) in the fused ring system may or may not have a fully delocalized pi-electron system. Examples of aryl groups include, but are not limited to, benzene, naphthalene and azulene.

As used herein, "heteroaryl" refers to a ring that contains one or more heteroatoms selected from the group consisting of nitrogen, oxygen and sulfur in the ring and that has a fully delocalized pi-electron system. The descriptor $C_3$-$C_{10}$ or $C_5$-$C_{10}$ refers to the number of carbon atoms, in addition to the necessary heteroatoms, in the system. The "heteroaryl" group can be made up of two or more fused rings (rings that share two adjacent carbon atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, but are not limited to, furan, thiophene, phthalazinone, pyrrole, oxazole, thiazole, imidazole, pyrazole, isoxazole, isothiazole, triazole, thiadiazole, pyran, pyridine, pyridazine, pyrimidine, pyrazine, indole, isoindole, isoquinoline and triazine.

As used herein, "alkyl" refers to a straight, branched chain, or cyclic fully saturated (no double or triple bonds) hydrocarbon (all carbon) group. An alkyl group of this invention may comprise from 1-6 carbon atoms, that is, designated as a "$C_1$ to $C_6$ alkyl." $C_1$ to $C_6$ alkyls are preferred. $C_1$ to $C_3$ alkyls are more preferred, and $C_1$ alkyl is most preferred. Examples of alkyl groups include, without limitation, methyl, ethyl, n-propyl, isopropyl, n-butyl, isobutyl, sec-butyl, tert-butyl, amyl, tert-amyl, hexyl, heptyl, octyl, nonyl, decyl, undecyl and dodecyl. Alkyl groups can be partially or fully fluorinated.

As used herein, "halo" and "halogen" refer to the fluoro, chloro, bromo or iodo atoms. Preferred halogens are chloro and fluoro.

Also as used herein, "alkoxy" refers to an "—O—R" group, where R represents alkyl, as defined above. Where two alkoxy groups are adjacent to one another, they may be alicyclic or together form a fused cyclic ring system, e.g.,

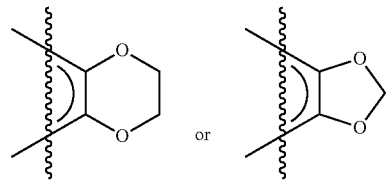

As used herein, "hydroxyl" refers to an "—OH" group, and those groups wherein the "—OH" group also contains a hydroxyl protecting group. As used herein, a "hydroxyl protecting group" refers to a readily cleavable group that replaces the hydrogen of the hydroxyl group, such as, without limitation, tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, and 2,2,2-trichloroethoxycarbonyl. The species of hydroxyl protecting groups is not critical so long as the derivatized hydroxyl group is stable to the conditions of subsequent reaction(s) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3, both of which are incorporated by reference herein for this purpose.

As used herein, "cyano" refers to a "—C≡N" group.

As used herein, "nitro" refers to an "—NO$_2$" group.

Throughout the present disclosure, when a particular compound comprises a chiral center, the scope of the present disclosure also includes compositions comprising the racemic mixture of the two enantiomers, as well as compositions comprising each enantiomer individually substantially free of the other enantiomer. Thus, for example, contemplated herein is a composition comprising the S enantiomer substantially free of the R enantiomer, or a composition comprising the R enantiomer substantially free of the S enantiomer. By "substantially free" it is meant that the composition comprises less than 10%, or less than 8%, or less than 5%, or less than 3%, or less than 1% of the minor enantiomer. If the particular compound comprises more than one chiral center, the scope of the present disclosure also includes compositions comprising a mixture of the various diastereomers, as well as compositions comprising each diastereomer substantially free of the other diastereomers. The recitation of a compound, without reference to any of its particular diastereomers, includes compositions comprising all four diastereomers, compositions comprising the racemic mixture of R,R and S,S isomers, compositions comprising the racemic mixture of R,S and S,R isomers, compositions comprising the R,R enantiomer substantially free of the other diastereomers, compositions comprising the S,S enantiomer substantially free of the other diastereomers, compositions comprising the R,S enantiomer substantially free of the other diastereomers, and compositions comprising the S,R enantiomer substantially free of the other diastereomers.

When a tautomer of the compound of the Formula I exists, embodiments of the present invention include any possible tautomers and pharmaceutically acceptable salts thereof, and mixtures thereof, except where specifically drawn or stated otherwise The disclosure and claims of the present invention are based on the known general principles of chemical bonding. It is understood that the claims do not encompass structures known to be unstable or not able to exist based on the literature.

Additional embodiments include those wherein Ar$_1$ and Ar$_2$ are each independently C$_6$-C$_{10}$ aryl or C$_3$-C$_{10}$ heteroaryl.

The invention also includes those compounds having a structure of Formula II or Formula III:

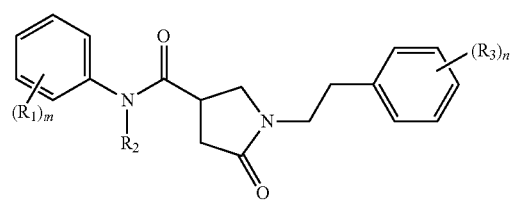

(II)

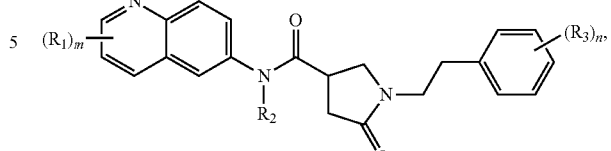

(III)

where m and n are independently 1 or 2.

In other embodiments, the present invention also includes those compounds having a structure of Formula IIA, IIIA, IVA, or IVB:

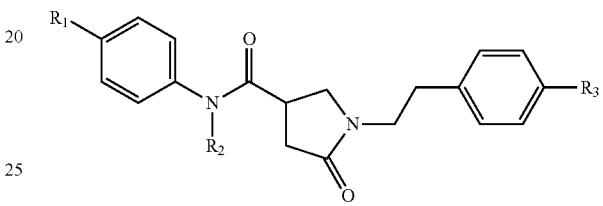

(IIA)

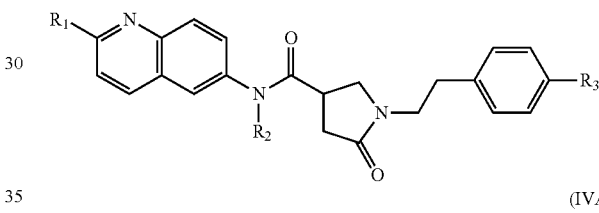

(IIIA)

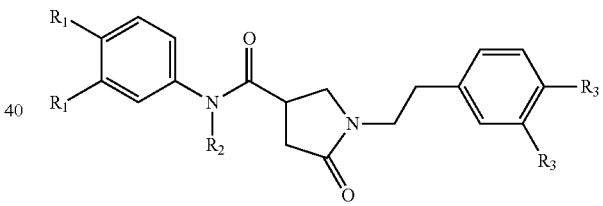

(IVA)

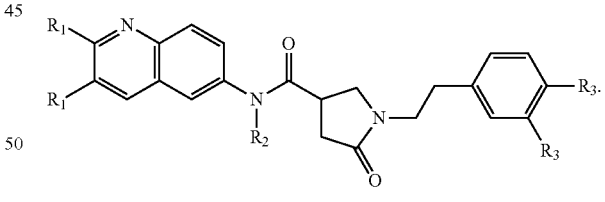

(IVB)

Additional embodiments include those wherein any of the preceding compounds specifically contain H in the R$_2$ position and/or where R$_3$ is independently halo, generally, and chloro or fluoro, specifically, at each occurrence.

Still additional embodiments include any or all of the preceding compounds R$_1$ is independently C$_{1-3}$ alkyl, halo, or C$_{1-3}$ alkoxy, at each occurrence.

Additional embodiments include those wherein any of the preceding compounds specifically contain H in the R$_2$ position and/or where R$_1$ is independently halo, generally, and chloro or fluoro, specifically, at each occurrence.

Still additional embodiments include any or all of the preceding compounds R$_3$ is independently C$_{1-3}$ alkyl, halo, or C$_{1-3}$ alkoxy, at each occurrence.

Other embodiments include the compounds having the structure of Formula B7, B7A, B7B, B7C, or B7G:
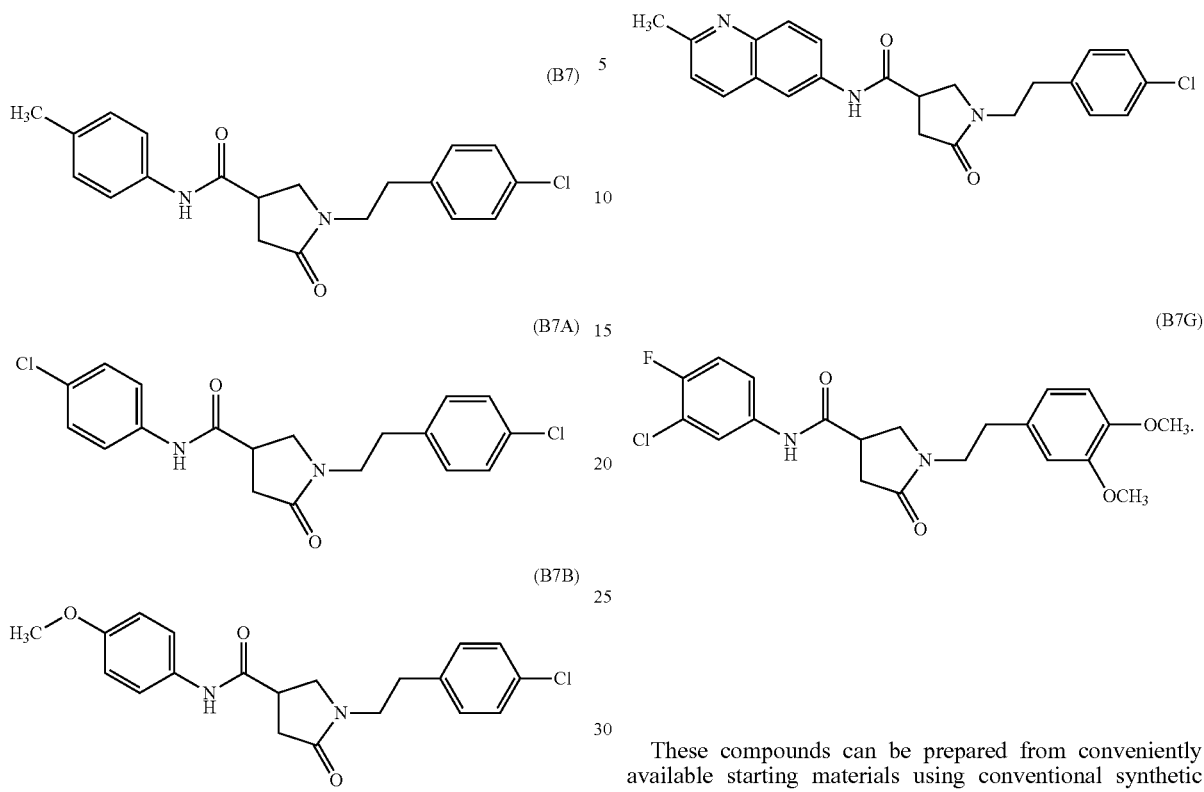
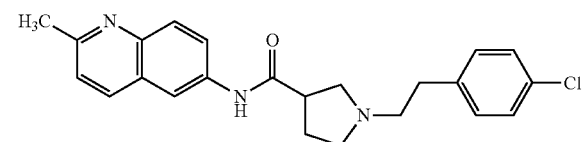
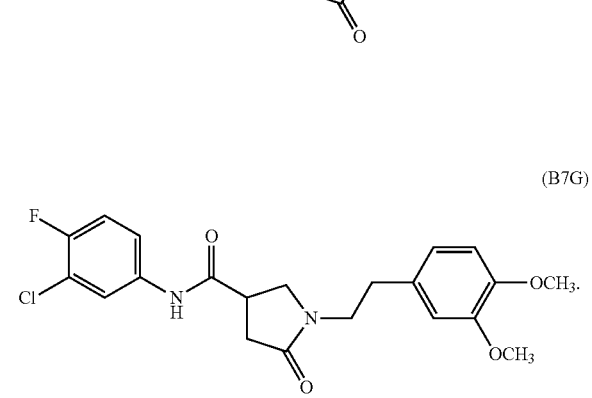
These compounds can be prepared from conveniently available starting materials using conventional synthetic methods (including step-wise nucleophilic substitution reactions) as exemplified by the following general scheme:
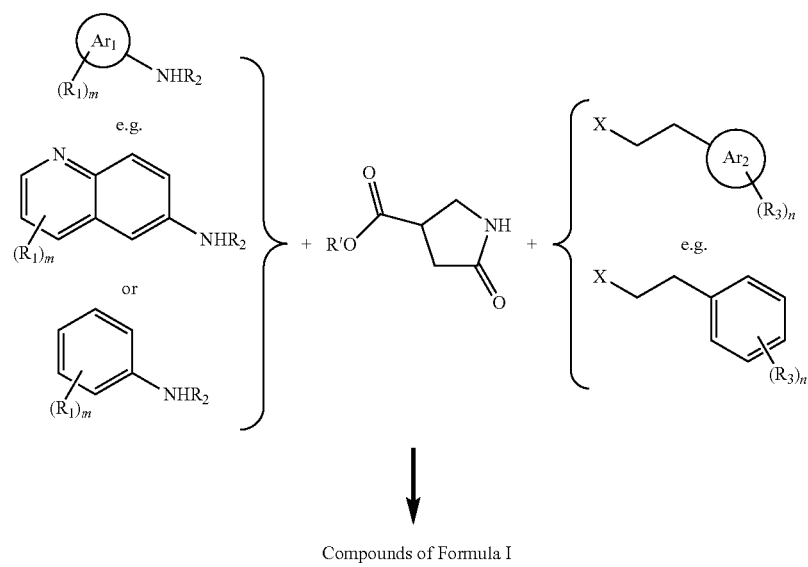
Compounds of Formula I (Note that reference to Compounds of Formula I also comprise all of the subgenera of species described above). A search of the internet shows that the raw materials, a number of intermediates, and some of the final product shown in this Scheme are, in fact, commercially available from a variety of commercial sources. The specific compounds B7, B7A, B7B, and B7C, for example, are available from Maybridge Chemical, part of Thermo Fisher Scientific, catalog numbers HTS10908 (B7); HTS10905 (B7A); HTS10906 (B7B) and HTS10909 (B7C). The compound identified as B7G is available from Enamine Ltd (Catalogue # T5337455).

The present invention also includes those embodiments of the compounds of Formula I themselves, excepting those specific compounds already known. That is, a pharmaceutically tolerable analog or homolog of a compound described herein as B7, B7A, B7B, B7C or B7G.

The present invention includes those pharmaceutical compositions comprising any one of the preceding compounds, as well as any pharmaceutically acceptable salt or solvate which may be derived from these compounds and their use in patient treatment. The term "pharmaceutically acceptable salt" means those salts of compounds of the invention that are safe and effective for use in a subject and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, and p-toluenesulfonate salts. Such salts may be prepared by contacting the base compound with the corresponding organic or inorganic acid.

Pharmaceutical compositions may be formulated in conventional manner using one or more physiologically acceptable carriers, diluents, excipients or auxiliaries which facilitate processing of the active compound into preparations which can be used pharmaceutically by one having ordinary skill in the art with compositions selected depending upon the chosen mode of administration. Such compositions are prepared in accordance with acceptable pharmaceutical procedures, such as described in Remingtons Pharmaceutical Sciences, 17th edition, ed. Alfonoso R. Gennaro, Mack Publishing Company, Easton, Pa. (1985) a standard reference text in this field, which is incorporated herein by reference. Pharmaceutically acceptable carriers are those that are compatible with the other ingredients in the formulation and biologically acceptable.

The pharmaceutical compositions of the present invention may be administered by any means that enables the active agent to reach the agent's site of action in the body of a mammal. Pharmaceutical compositions may be administered orally or parenterally, i.e., intratumor, intravenous, subcutaneous, intramuscular, etc. The compounds of this invention may be administered neat or in combination with conventional pharmaceutical carriers, the proportion of which is determined by the solubility and chemical nature of the compound, chosen route of administration and standard pharmacological practice. The pharmaceutical carrier may be solid or liquid.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents.

For topical administration the compounds of the invention may be formulated as gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999), which is incorporated by reference in its entirety.

Formulations for topical administration may be formulated to be immediate and/or modified release. Modified release formulations include delayed-, sustained-, pulsed-, controlled-, targeted and programmed release.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hanks solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be administered by, for example, intramuscular, intraperitoneal or subcutaneous injection. Sterile solutions can also be administered intravenously. Oral administration may be either liquid or solid composition form.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

The compounds of this invention may be administered rectally or vaginally in the form of a conventional suppository, pessary, or enema. Cocoa butter is a traditional suppository base, but various alternatives may be used as appropriate.

For administration by intranasal or intrabronchial inhalation or insufflation, the compounds of this invention may be formulated into an aqueous or partially aqueous solution, or as a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 .mu.L to 100 μL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

Pharmaceutical compositions suitable for use in the methods disclosed herein include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. The dosage requirements vary with the particular compositions employed, the route of administration, the severity of the symptoms presented and the particular subject being treated. Based on the results obtained in the standard pharmacological test procedures, projected daily dosages of active compound would be 0.02 μg/kg-750 μg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated.

Certain aspects of the present invention teach methods of treating a patient in need thereof comprising administering a pharmaceutically effective amount of at least one compound of Formula I. As used within the following discussion, the term "at least one compound of Formula I" is intended to include all the specific embodiments described previously in the specification as relating to the genus and species of the compound of Formula I, as well as corresponding pharmaceutical compositions, salts and solvates.

The term "administering" in the context of administering a compound refers to any or all of the steps including preparing a formulation, as discussed herein, containing the compound being administered; prescribing or indicating the need to take the compound being administered; providing a composition containing the compound being administered; and/or ingesting by or applying to a subject or a cell or organ within the subject, by any known method. For example, a solution containing the compound can be injected to the subject or be added to the medium containing the cells, or the subject can orally ingest a formulation containing the compound. The term "contacting" refers to bringing the subject or the cell into contact with the compound. Thus, a formulation of a prodrug can be administered to a subject, whereupon the prodrug undergoes metabolism. The metabolite is then either in the systemic circulation or within the cytoplasm. In this situation, the prodrug is "administered" to the subject, but both the subject and the cells are "contacted" with the metabolite.

The term "treating" or "treatment" does not necessarily mean total cure. Any alleviation of any undesired signs or symptoms of the disease to any extent or the slowing down of the progress of the disease can be considered treatment. Furthermore, treatment may include acts that may worsen the patient's overall feeling of well-being or appearance. Treatment may also include lengthening the life of the patient, even if the symptoms are not alleviated, the disease conditions are not ameliorated, or the patient's overall feeling of well-being is not improved.

Similarly, the term "preventing" does not require total prevention of a disease or condition, but also includes the inhibition or regression of progress of the disease or condition said to be prevented.

In certain aspects, disclosed herein are methods of treating a disorder in a subject comprising administering to the subject a therapeutically effective amount of at least one compound of Formula I. Said embodiments may also include identifying the subject in need of such treatment, though the invention is intended to encompass the effect of the administration and not necessarily the conscious intent of the administrator. The disorders include autoimmune disorders that is caused by a lack, deficiency, or underperformance of functional suppressor T cells. Specific examples of disorders of the present invention include multiple sclerosis, diabetes mellitus, rheumatoid arthritis, lupus, Crohn's disease, Hashimoto's disease, polymyositis, inflammatory bowel disease, colitis, scleroderma, oophoritis, thyroiditis, Grave's disease, dermatomyositis, pemphigus vulgaris, myasthenia gravis, hemolytic anemia, or Sjogren's disease, and especially Crohn's disease, inflammatory bowel disease, or colitis.

Data from NIH, the American Autoimmune Related Diseases Association and elsewhere indicate that ~24 million Americans live with one or more types of the currently 80-100 recognized autoimmune diseases (10-12). Autoimmunity costs the nation $86 billion/year. Moreover, ~75% of cases of autoimmune diseases occur in women, and autoimmune diseases are the $4^{th}$ largest cause of disability among US women. Broken down further, autoimmune thyroiditis affects 40/1000 American women, psoriasis affects >20/1000 Americans, rheumatoid arthritis affects about 10/1000 Americans, SLE affects 4/1000 young African-American women, and IBD, multiple sclerosis and type I diabetes each affect ~1.5/1000 Americans. On a smaller scale, there are also important unmet needs in terms of regulation of immunity in transplant recipients, with 27,578 patients receiving organ transplants in 2007, and 173,339 patients currently living with a functional organ transplant (UNOS data). Even with complex current immunosuppressive regimens, 5-year graft survival rates are 68% for cadaveric donor kidneys and 73% for heart grafts, and there are high rates of toxicity associated with these protocols. These areas of autoimmunity and transplantation are further interrelated in that autoimmune diseases are a major cause of endstage organ failure requiring transplantation (e.g. kidney, liver), and some forms of endstage autoimmunity would be treated by tissue transplantation if less toxic immunosuppressive regimens were available so as to control transplant rejection without having a major negative impact on the host (e.g. islet grafts for type 1 diabetes). It is envisioned that the treatments described in the present invention can be used to treat these ailments or conditions.

In certain embodiments, the at least one compound of Formula I is administered remedially, after the development of the disease. In other embodiments, the at least one compound of Formula I is administered prophylatically, before the development of the disease, for example, in subjects otherwise at risk of developing the disease or condition, whether that risk is caused by genetics, injury, or other circumstance.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", Ch. 1 p. 1). Typically, the dose about the composition administered to the patient can be from about 0.5 to 1000 mg/kg of the patient's body weight, or 1 to 500 mg/kg, or 10 to 500 mg/kg, or 50 to 100 mg/kg of the patient's body weight. The dosage may be a single one or a series of two or more given in the course of one or more days, as is needed by the patient. Note that for almost all of the specific compounds mentioned in the present disclosure, human dosages for treatment of at least some condition have been established. Thus, in most instances, the methods disclosed herein will use those same dosages, or dosages that are between about 0.1% and 500%, or between about 25% and 250%, or between 50% and 100% of the established human dosage. Where no human dosage is established, as will be the case for newly discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals. For systemic administration, a therapeutically effective dose can be estimated initially from in vitro assays.

Although the exact dosage will be determined on a drug-by-drug basis, in most cases, some generalizations regarding the dosage can be made. The daily dosage regimen for an adult human patient may be, for example, an oral dose of between 0.1 mg and 500 mg of each ingredient, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions disclosed herein or a pharmaceutically acceptable salt thereof calculated as the free base, the composition being administered 1 to 4 times per day. Alternatively the compositions disclosed herein may be administered by continuous intravenous infusion, preferably at a dose of each ingredient up to 400 mg per day. Thus, the total daily dosage by oral administration of each ingredient will typically be in the range 1 to 2000 mg and the total daily dosage by parenteral administration will typically be in the range 0.1 to 400 mg. Suitably the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, preferably between 30-90% and most preferably between 50-90%.

In cases of local administration or selective uptake, the effective local concentration of the drug may not be related to plasma concentration. One having skill in the art will be able to optimize therapeutically effective local dosages without undue experimentation.

The amount of composition administered will, of course, be dependent on the subject being treated, on the subject's weight, the severity of the affliction, the manner of administration and the judgment of the prescribing physician.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

A co-pending application, U.S. patent application Ser. No. 12/161,192, published as U.S. Patent Application Publication US 2010/0061984, which is incorporated by reference herein, describes other compositions and methods for modulation of suppressor T cell activation. It is envisioned that the present compositions and treatment options may complement those described in this application, and may also be used as described therein.

EXAMPLES

Example 1

TIP60/p300/FOXP3 Interactions

Figure 4:
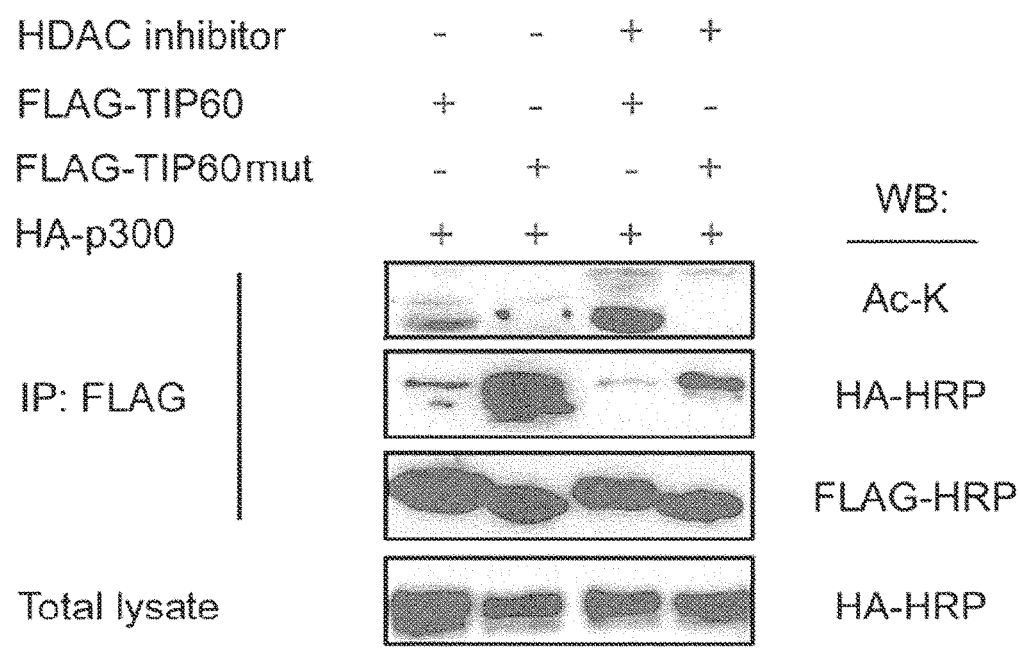
FIG. 4. are Western blot plots showing that p300 promotes TIP60 auto-acetylation, and in turn decreases interaction of TIP60 and p300. 293T cells were cotransfected with p300 and TIP60 or TIP60 mutant. After 24 h, cells were treated with HDACi (400 nM TSA & 10 mM NAD) for 4 h. Cell lysates were analyzed by Western blot using HA-HRP (lowest panel), or immunoprecipitated with anti-FLAG, followed by blotting with acetyl-lysine (first panel), HA-HRP (second panel) or FLAG-HRP (third panel). The plots show particularly the co-precipitation (and so complexation) of the TIP60mut and p300 when present together.
Figure 5:
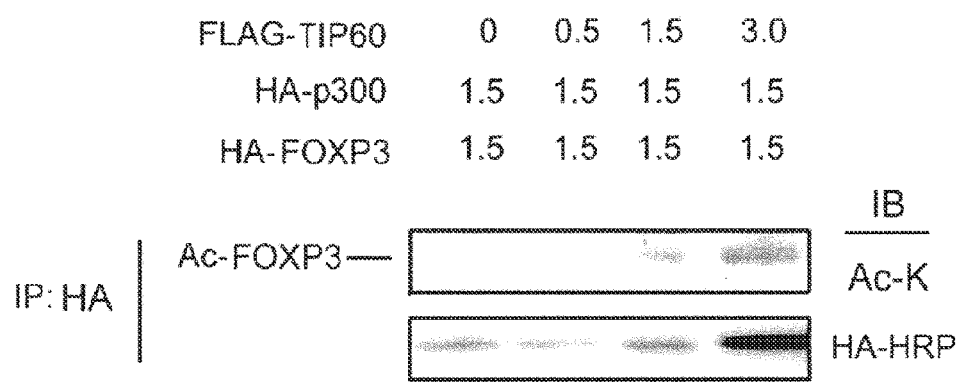
FIG. 5. show that TIP60 and p300 cooperate to promote FOXP3 acetylation. 293T cells were cotransfected with constant amount of FOXP3 & p300, and increasing amounts of TIP60, then immunoprecipitated with anti-HA, followed by western blot using acetylated-lysine (upper) or HA-HRP (lower).
Figure 6:
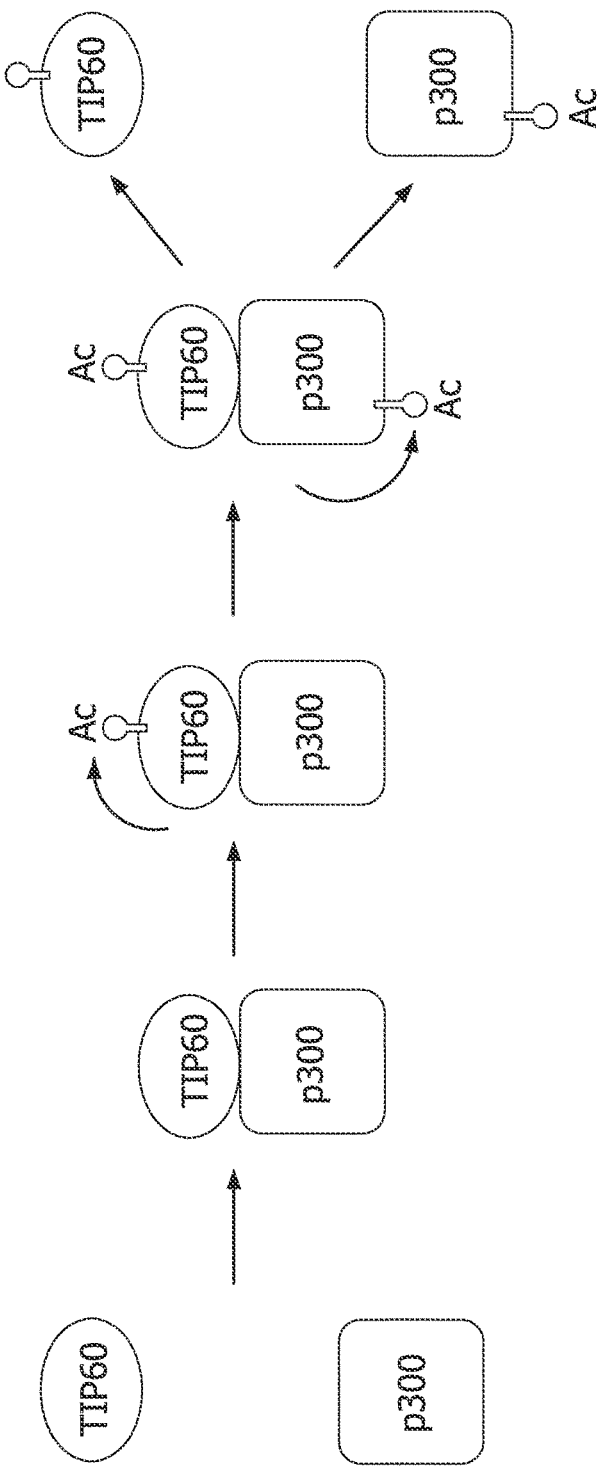
FIG. 6. show cooperative TIP60/p300 interactions that dynamically regulate the HAT activity of p300 and subsequently the extent of FOXP3 acetylation. Lysine acetylation is shown by the label "Ac".

The data in FIG. 4 through FIG. 6 show that both TIP60 of the MYST family and p300 of the p300/CBP family positively regulate the acetylation of FOXP3. These proteins, upon activation by discrete extrinsic signals, act to regulate the acetylation levels of FOXP3. Acetylation is also required for the HAT activity of TIP60 and p300, a process that is achieved either by auto-acetylation or as a result of acetylation by other HATs. Both TIP60 and p300 are more active in their acetylated forms, and p300 promotes the acetylation level of TIP60. Using an enzymatic deficient form of TIP60, this TIP60 mutant was found not to be acetylated even in the presence of p300, indicating that p300 actually promotes TIP60 auto-acetylation. Interestingly, the interaction of TIP60 and p300 is then decreased when TIP60 is acetylated (FIG. 4). While TIP60 and p300 were both shown to acetylate FOXP3, TIP60 and p300 cooperate with each other to promote their acetylation level and thus facilitating FOXP3 acetylation. Indeed when FOXP3 is present in low level, neither p300 nor TIP60 alone is sufficient to lead to high levels of FOXP3 acetylation. However, when TIP60 and p300 are combined, strong FOXP3 acetylation was observed (FIG. 5), indicating synergy of TIP60 and p300 in promoting FOXP3 acetylation. These events are modeled in FIG. 6.

Example 2

TIP60 Inhibition by Genetic Means

Figure 7:
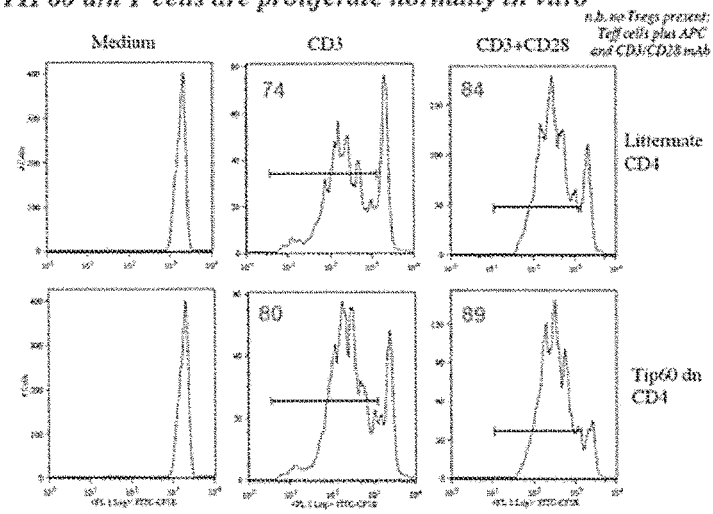
FIG. 7 show a characterization of TIP60dn mouse (indicative of how effective an ideal TIP60 inhibitor small molecule might be).
Figure 7:
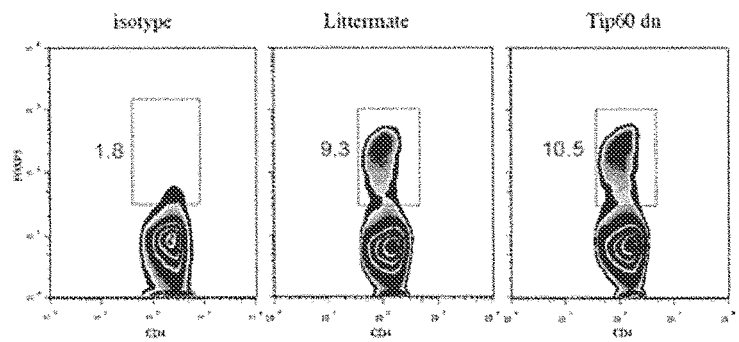
Figure 7:
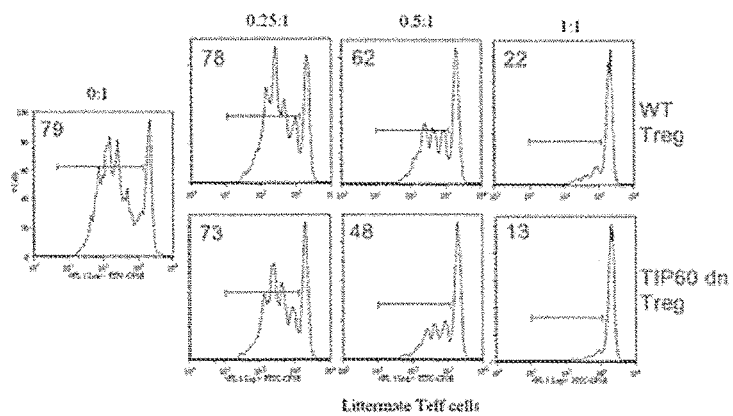

As a prelude to seeking pharmacologic inhibitors of TIP60 (TIP60i), TIP60 dominant-negative (TIP60dn) mice were developed in which key residues in the active site of TIP60 were mutated so as to remove catalytic activity. TIP60dn mice are healthy, breed normally, are not prone to infections or tumors, but have no TIP60 catalytic activity when assessed using in vitro assays (data not shown). As shown in FIG. 7, T cells from these mice proliferate normally upon CD3/CD28 mAb-induced activation in the absence of Tregs (top panel). These mice also have normal numbers of FOXP3+CD4+ Tregs (middle panel). However, Tregs isolated form these mice have markedly enhanced Treg function, as shown (lower panel) using standard Treg suppression assays. TIP60dn mice appear normal but their Tregs have enhanced suppressive activity in vitro (and in vivo, as shown below).

Example 3

Screening of Pharmacologic TIP60 Inhibitors

Several exemplary compounds of the present invention were screened at 10 µg/ml in vitro, at varying Treg:T cell ratios, using standard cell proliferation techniques (3 days, using CSFE dyes). Such techniques are well understood by those skilled in the art. For example, see Akimova T, Ge G, Golovina T, Mikheeva T, Wang L, Riley J L, Hancock W W., "Histone/protein deacetylase inhibitors increase suppressive functions of human FOXP3+ Tregs," Clin Immunol. 2010 September; 136(3):348-63; Tao R, Hancock W W., Resistance of FOXP3+ regulatory T cells to Nur77-induced apoptosis promotes allograft survival," PLoS One. 2008 May 28; 3(5):e2321; Tao R, Wang L, Murphy K M, Fraser C C, Hancock W W., "Regulatory T cell expression of herpesvirus entry mediator suppresses the function of B and T lymphocyte attenuator-positive effector T cells.," J. Immunol. 2008 May 15; 180(10):6649-55; and Tao R, de Zoeten E F, Ozkaynak E, Chen C, Wang L, Porrett P M, Li B, Turka L A, Olson E N, Greene M I, Wells A D, Hancock W W., "Deacetylase inhibition promotes the generation and function of regulatory T cells," Nat. Med. 2007 November; 13(11):1299-307 for the protocols used herein. Each of these references is incorporated by reference herein, at least for this purpose.

Figure 8A:
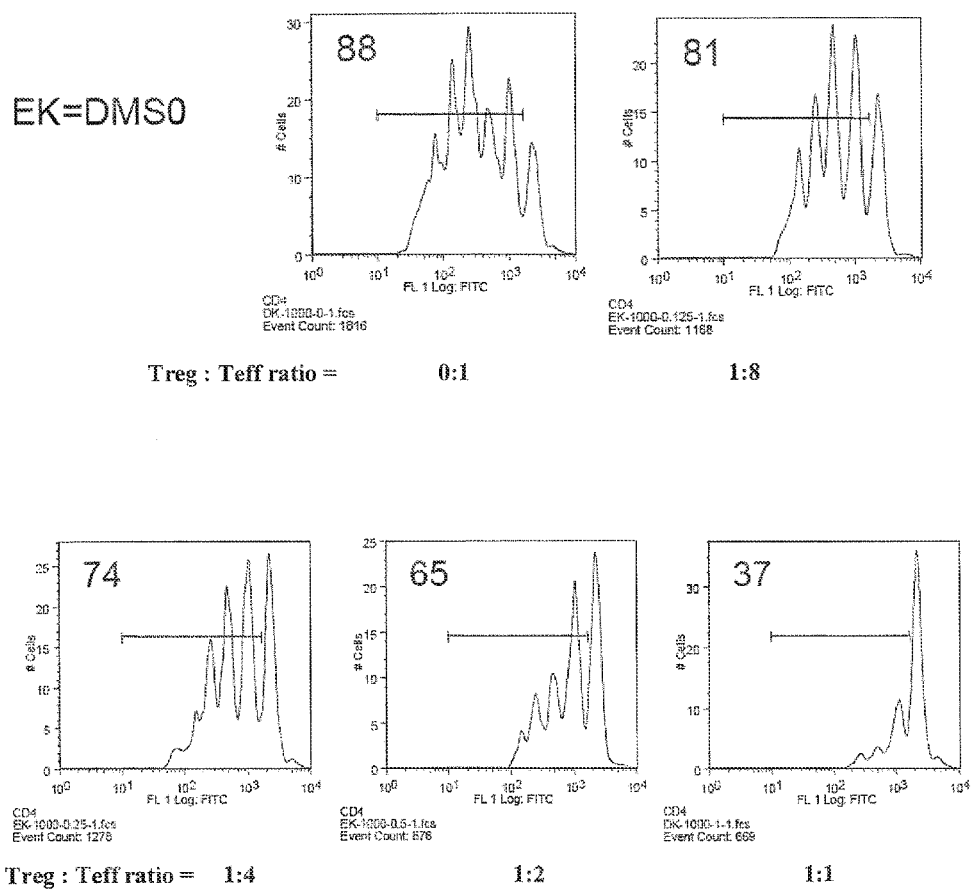
FIGS. 8A-D are flow cytometry dataplots showing the enhancement of TIP60 inhibitor B7 suppression of Treg in vitro. Individual peaks reflect number of cells divisions under the standard test conditions (3 days), where the cell populations are dyed with CFSE (carboxyfluorescen diacetate, succimidyl ester).
Figure 8B:
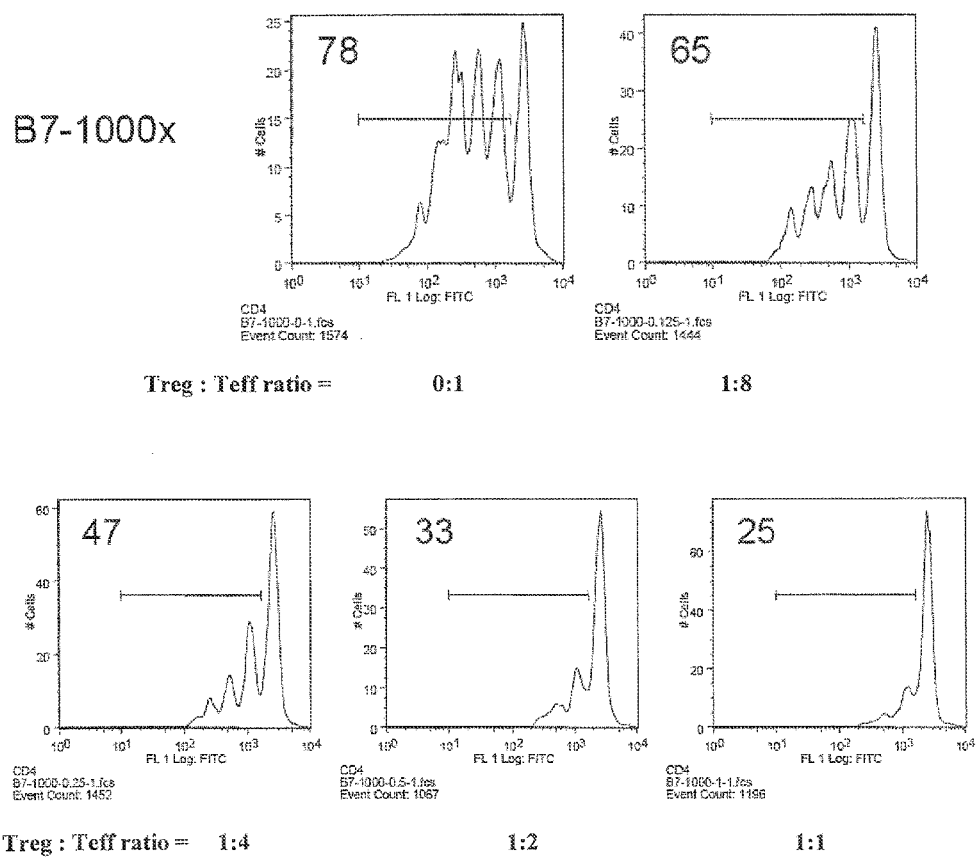
Figure 8C:
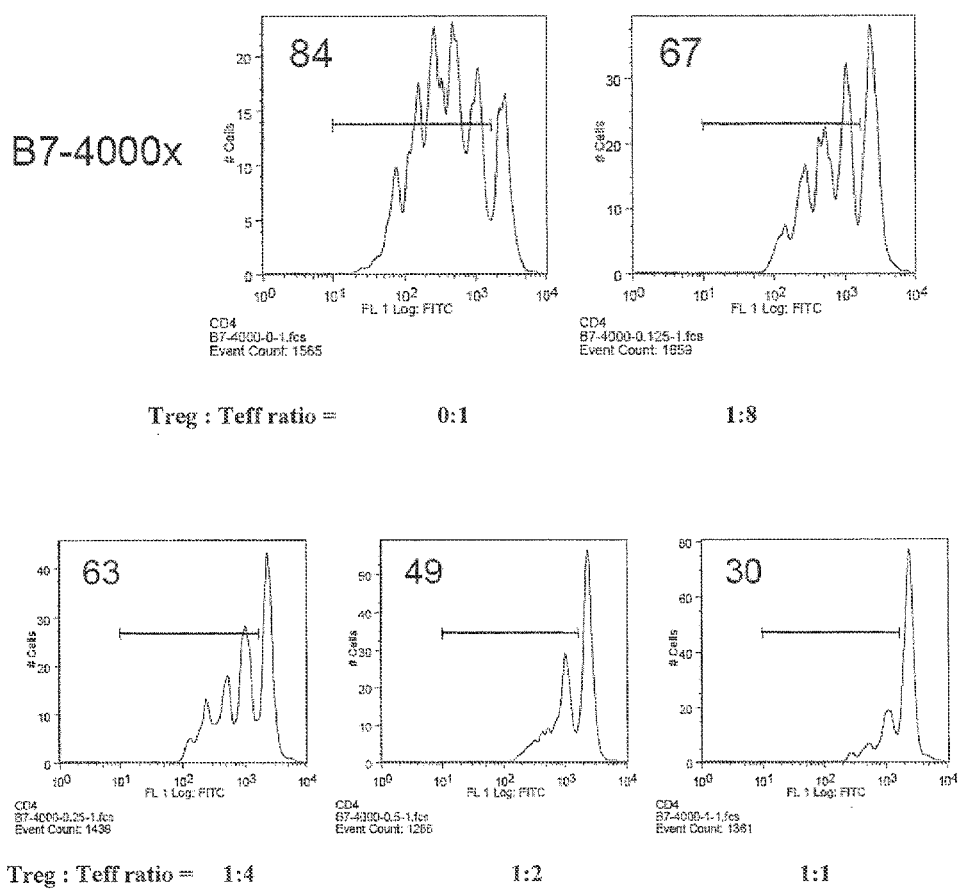
Figure 8D:
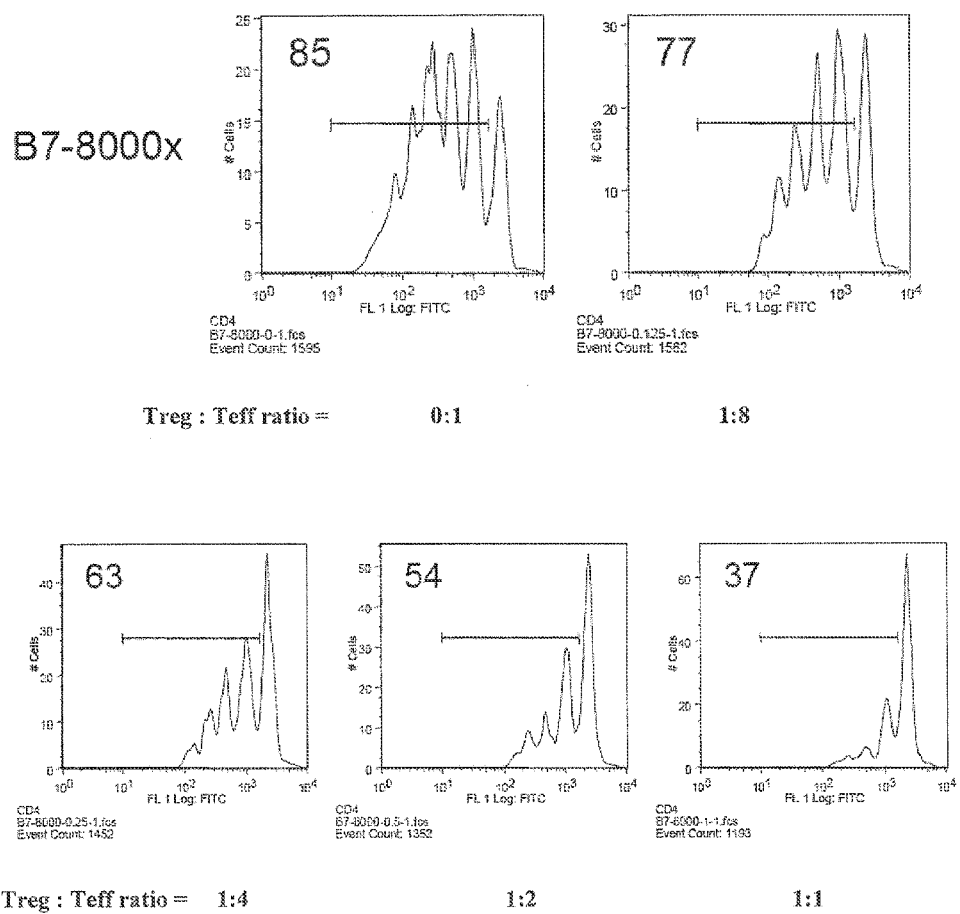
Figure 9:
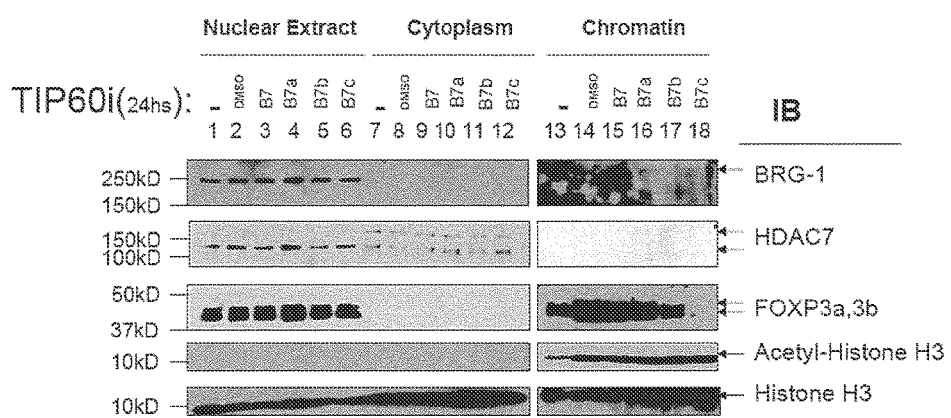
FIG. 9. are Western blot dataplots showing B7c intervening with FOXP3 bound on chromatin in SZ-4 T cells.
Figure 10A:
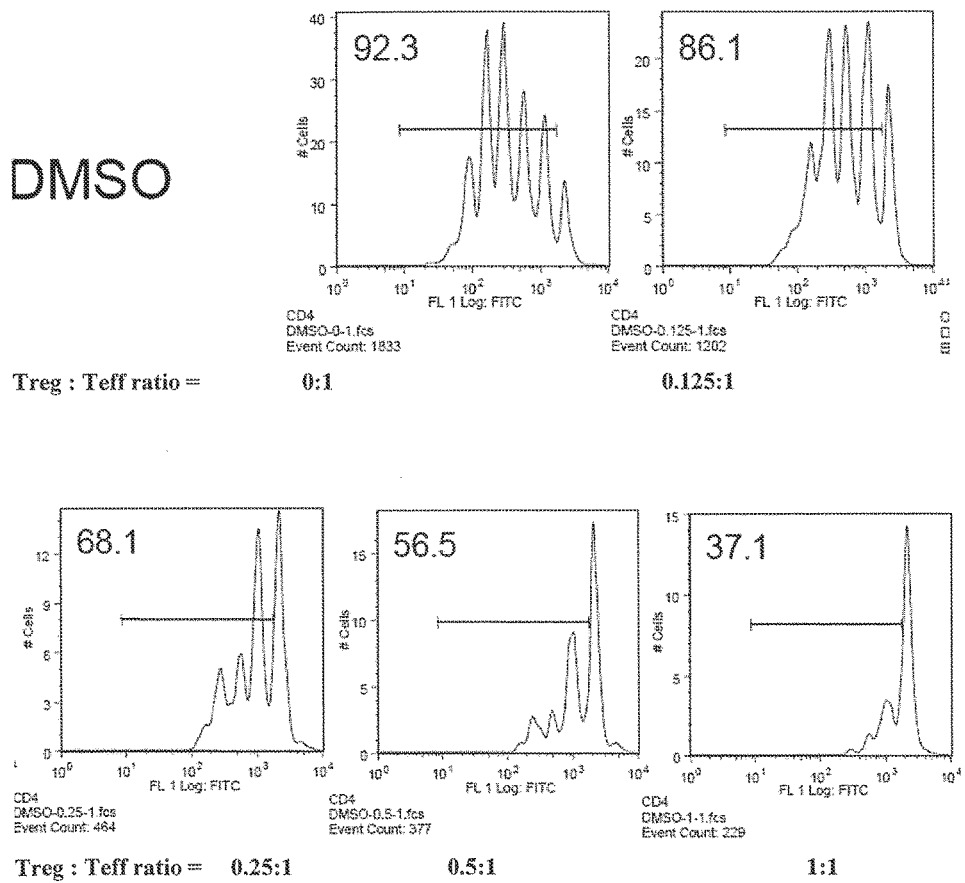
FIGS. 10A-E are flow cytometry dataplots showing the enhancement of TIP60 inhibitors B7 suppression of Treg in vitro.
Figure 10B:
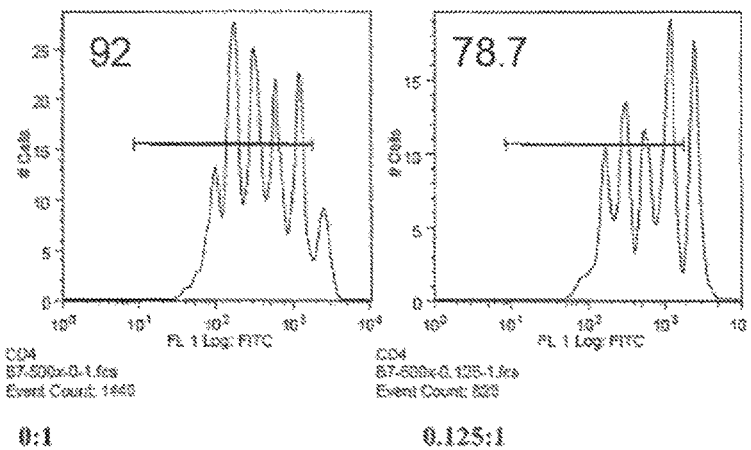
Figure 10B:
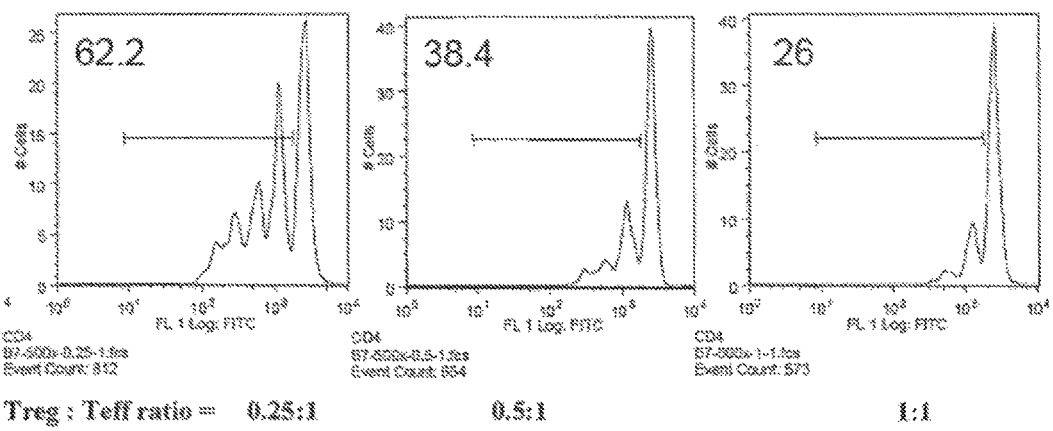
Figure 10C:
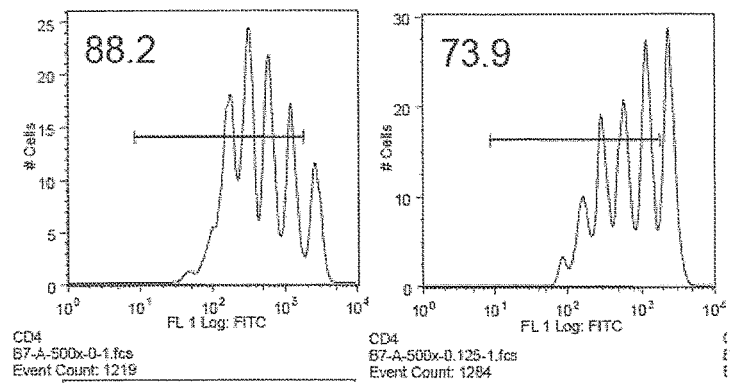
Figure 10C:
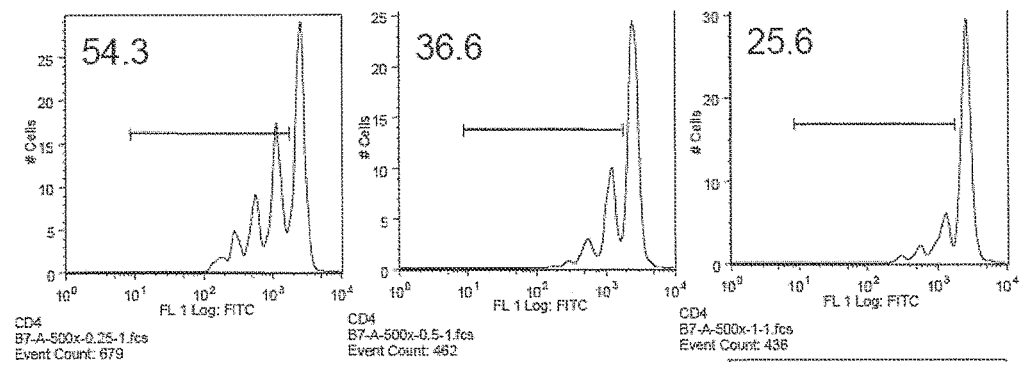
Figure 10D:
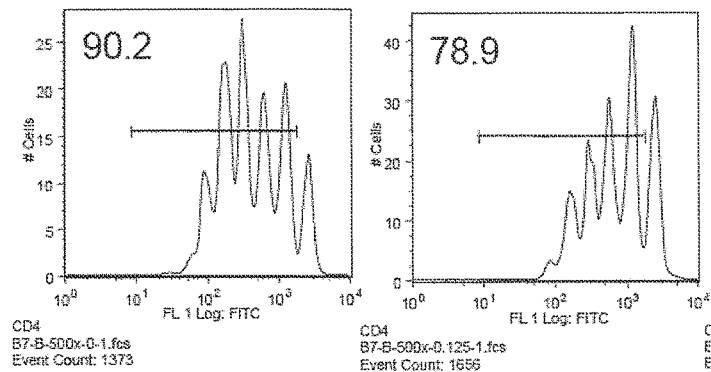
Figure 10D:
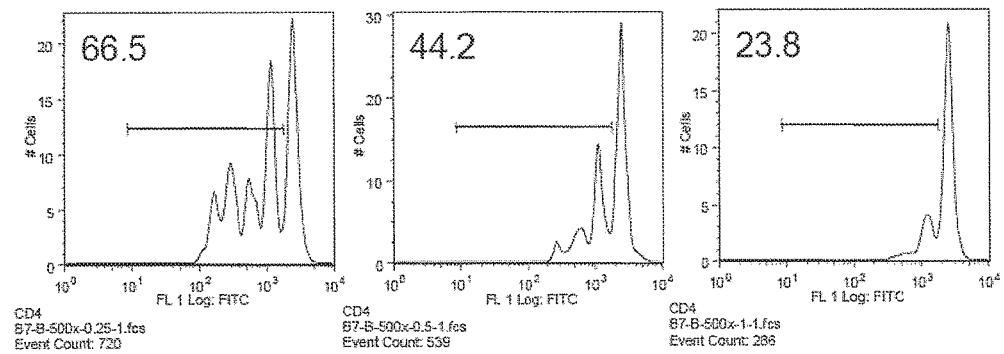
Figure 10E:
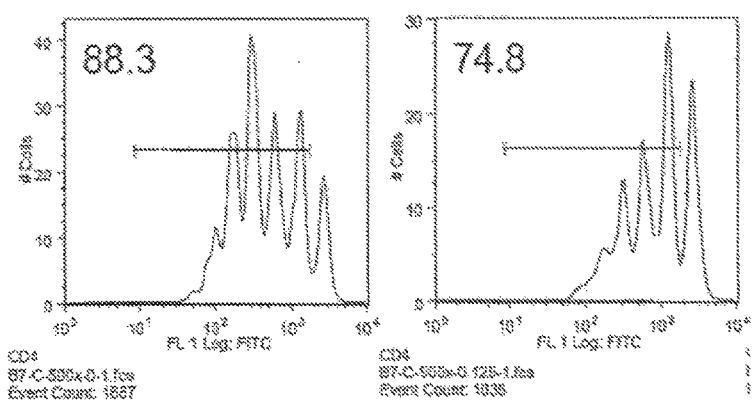
Figure 10E:
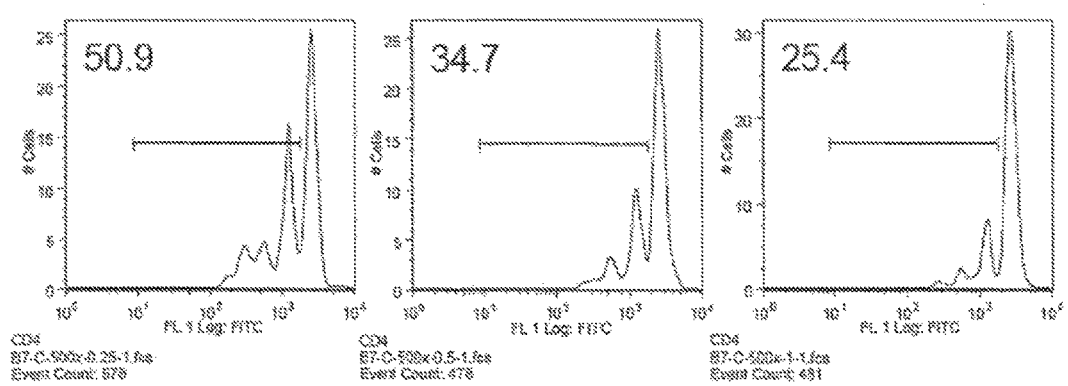

T cell proliferation was unimpaired in the absence of Treg cells (see left panels in FIG. 8A-D), but was increasingly impaired at increasing Treg concentration (for example, in FIG. 8A, increasing Treg:Tcell ratio from 0:1 to 1:1 reduced proliferation from 88% to 37% under otherwise identical conditions). The addition of B7 enhanced the Treg activity (decreasing Tcell proliferation) in a dose dependent manner (for example, compare the effect of increasing B7 dosages in FIGS. 8D-B, from 2.5 to 10 µM, on cell proliferation at Treg:Teff=1:1, decreasing from 37% to 30% to 25%). Similar effects were seen with the other compounds studied (e.g., FIG. 10A-10E). Efficacy was also seen at 1 µg/ml for some compounds.

Example 4

Inhibition of TIP60 Activity by B7G

Figure 11:
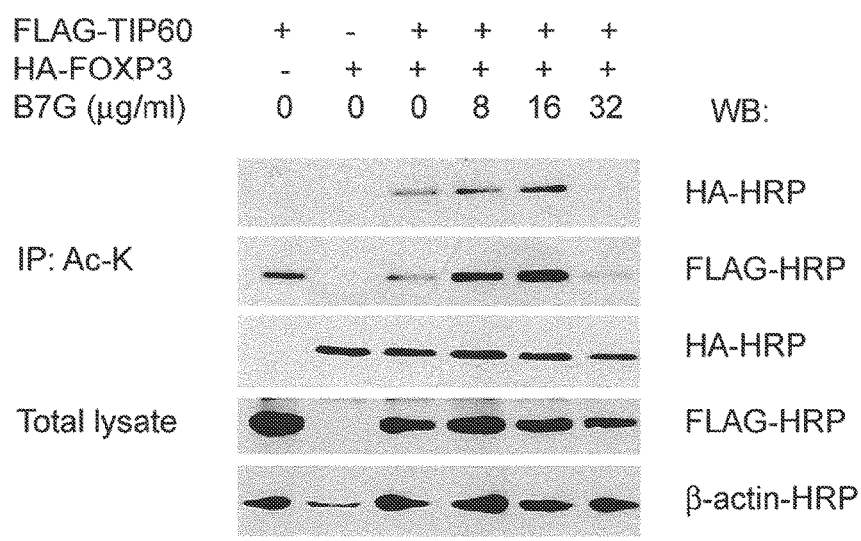
FIG. 11 illustrate the effect of B7G on TIP60. TIP60 activity was assessed by examining acetylation of TIP60 or its substrate FOXP3. Both TIP60 and FOXP3 were overexpressed in 293T cells. Acetylated proteins were first immunoprecipitated with the acetyl-lysine specific antibody Ac-K and then blotted with HRP conjugated antibodies to expression tags (HA for FOXP3 or FLAG for TIP60).

TIP60 is known to have acetyl transferase activity to acetylate itself (auto-acetylation) or substrates including FOXP3. To examine activity of B7G on TIP60, 293T cells were transfected with Flag-tagged TIP60 and HA-tagged FOXP3. 24 hours after transfection, cells were treated with various concentrations of B7G for 4 hours before cell lysates were collected. Acetylated proteins were precipitated by anti-acetyl lysine antibody Ac-K. FOXP3 and TIP60 in the lysate or precipitated by Ac-K antibody were identified by anti-HA-HRP and anti-FLAG-HRP respectively. As shown in FIG. 11, analysis of total cell lysates indicated that FOXP3 and TIP60 expression levels were not significantly affected by B7G (see "Total lysate", HA-HRP and FLAG-HRP panels). Acetylated FOXP3 and Acetylated TIP60, as indicated by the HA-HRP and FLAG-HRP blots from Ac-K precipitated proteins, were reduced significantly when cells were treated with 32 μg/ml B7G. At lower concentration, B7G appeared to slightly increase TIP60 auto-acetylation.

Example 5

TIP60 Targeting In Vivo Using Murine IBD Models (FIG. 12)

The TIP60dn mice were used to assess the performance of several TIP60 inhibitors, and data were generated in 2 different IBD models with these mice.

In a first test, the effects of exposure to dextran sodium sulfate (DSS) were evaluated, which results in a partially CD4-dependent inflammatory model of colitis, in wildtype (WT) versus TIP60dn C57BL/6 mice (8 mice/group). TIP60dn mice showed a marked resistance to development of colitis, with decreased histologic evidence of colitis (p=0.005), as seen in FIG. 12A. Also reflective of this inflammation, preliminary data showed significantly reduced colon lengths for the DMSO control animals (mean lengths=52.7 mm) vs. the TIP60dn mice (mean lengths=64.3 mm) after 21 days of treatment (p=0.0019).

Additionally, in a rigorously T cell-dependent model of colitis, purified CD45RBhi Tcells were adoptive transferred into immunodeficient mice. Co-administration of TIP60dn Tregs markedly attenuated the development of colitis compared to use of WT Tregs, as shown histologically (p=0.008) in FIG. 12B. Also reflective of this inflammation, preliminary data showed significantly reduced colon lengths for the animals subjected to co-administered Tcells plus WT Tregs (mean lengths=52.7 mm) vs. the mice co-administered with Tcells plus TIP60dn Tregs (mean lengths=64.3 mm) (p=0.0012). The fully T cell-dependent adoptive transfer model of colitis lasted 75-100 days, since the onset of disease post-transfer varies.

Data were also generated using the compound of Structure B7 in the DSS model, in an experiment designed to test the ability of TIP60 inhibitor therapy to reverse established colitis by waiting until mice had ~15% weight loss. In marked contrast to use of carrier DMSO alone, TIP60 inhibitor therapy (2 mg/kg/d, i.p.) reversed weight loss (p<0.01), blood in the stool (p<0.01) and diarrhea (p<0.005) (see FIG. 12C) and maintained colon length (p<0.01). The colon of a single animal treated with 3% DSS, then B7 according to this regimen, had a length about 94% of that of an unstressed control animal, whereas the length of the colon of an animal stressed by the 3% DSS but not remediated by B7 was about 85% of control. Likewise, the spleen of the remediate animal was comparable in size to that of the control, whereas the spleen of the unremediated animal was about 3-4 times as large as that of the control animal.

As a result of these experiments, the skilled artisan can conclude that TIP60 targeting can prevent development of colitis (Colitis 1 panel) and protective effects can be linked solely to the effects on Treg expression of reduced TIP60 activity (Colitis 2 panel). In addition, markedly beneficial effects are seen using the TIP60 inhibitors once disease has been induced (Colitis 3 panel); i.e. the molecules of the present invention can be used to treat colitis.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or method may be used in combination with any other material, feature, or method.

The disclosures of each patent, patent application, and publication cited or described in this document are hereby incorporated herein by reference, in their entirety, for all purposes.

What is claimed:

1. A pharmaceutical composition comprising a compound having a structure of Formula I:

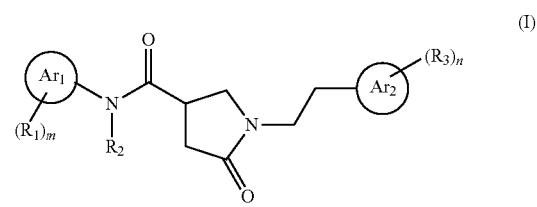

wherein $Ar_1$ and $Ar_2$ are each independently phenyl, pyridinyl, naphthyl, or quinolinyl;

$R_1$ and $R_3$ are each independently at each occurrence alkyl, halo, hydroxyl, cyano, nitro, or alkoxy;

$R_2$ is H or alkyl; and m and n are independently 0, 1, or 2;

and at least one pharmaceutically acceptable carrier, diluent, excipient or auxiliary, said composition formulated in a unit dosage form suitable for oral administration, parenteral administration, rectal administration, topical administration, or vaginal administration to a mammal, wherein:

(a) the dosage form suitable for oral administration is a tablet capsule or lozenge;

(b) the dosage form suitable for parenteral administration comprises an aqueous solution selected from the group consisting of Hanks solution, Ringer's solution and a physiological saline buffer, and further optionally containing one or more emulsifying agents and/or suspending agents;

(c) the dosage form suitable for topical administration is a gel, lotion, cream, ointment foam, skin patch, wafers, or implant; and (d) the dosage form suitable for rectal or vaginal administration is a suppository or pessary; and wherein the compound having a structure of Formula I is present in a therapeutically effective amount for treating multiple sclerosis, diabetes mellitus, rheumatoid arthritis, lupus, Crohn's disease, Hashimoto's disease, polymyositis, inflammatory bowel disease, colitis, scleroderma, oophoritis, thyroiditis, Grave's disease, dermatomyositis, Pemphigus vulgaris, myasthenia gravis, hemolytic anemia, or Sjogren's disease.

2. The pharmaceutical composition of claim 1, wherein compound is present in the dosage form in an amount sufficient to inhibit HAT activity or expression.

3. The pharmaceutical composition of claim 1, wherein $Ar_1$ is phenyl.

4. The pharmaceutical composition of claim 1, wherein the compound has a structure of Formula II or Formula III:

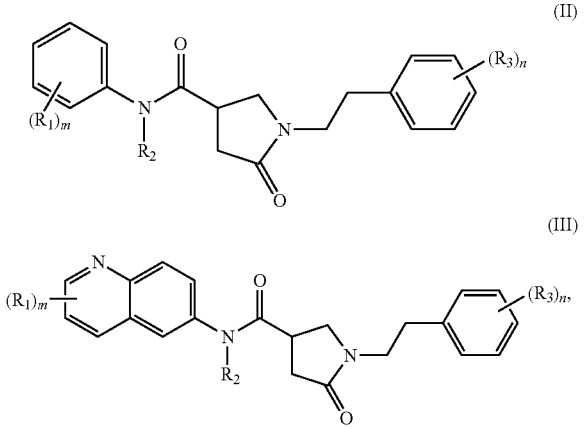

where m and n are independently 1 or 2.

5. The pharmaceutical composition of claim 1, wherein the compound has a structure of Formula IIA, IIIA, IVA, or IVB:

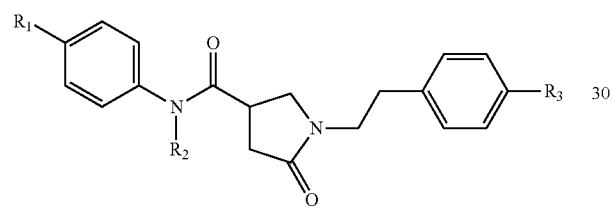

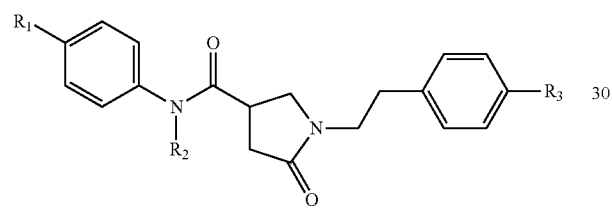

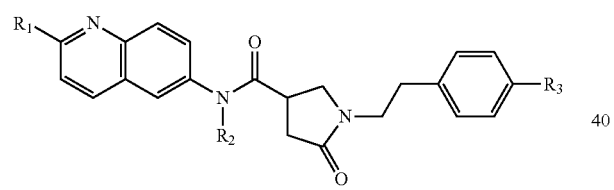

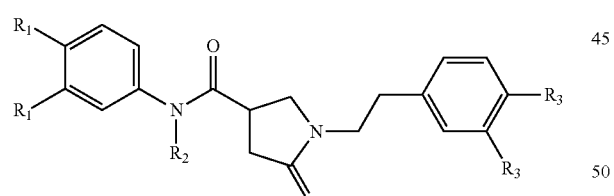

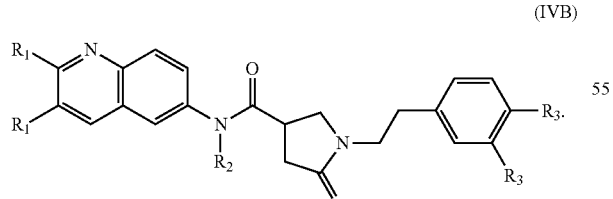

6. The pharmaceutical composition of claim 1, wherein $R_2$ is H.

7. The pharmaceutical composition of claim 1, wherein $R_3$ is independently halo at each occurrence.

8. The pharmaceutical composition of claim 1, wherein $R_3$ is independently at each occurrence chloro or fluoro.

9. The pharmaceutical composition of claim 1, wherein $R_1$ is independently at each occurrence $C_{1-3}$ alkyl, halo, or $C_{1-3}$ alkoxy.

10. The pharmaceutical composition of claim 1, wherein $R_1$ is independently at each occurrence halo.

11. The pharmaceutical composition of claim 10, wherein $R_1$ is independently at each occurrence chloro or fluoro.

12. The pharmaceutical composition of claim 10, wherein $R_3$ is independently at each occurrence $C_{1-3}$ alkyl, halo, or $C_{1-3}$ alkoxy.

13. The pharmaceutical composition of claim 1, wherein the compound has a structure of Formula B7, B7A, B7B, B7C, or B7G:

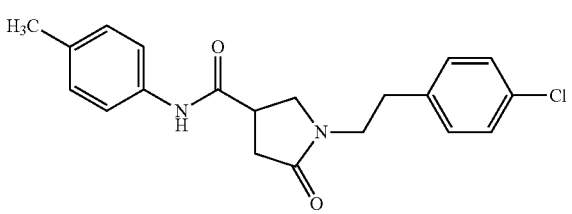

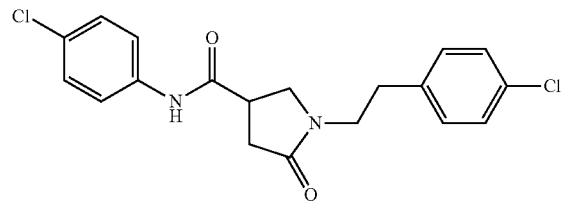

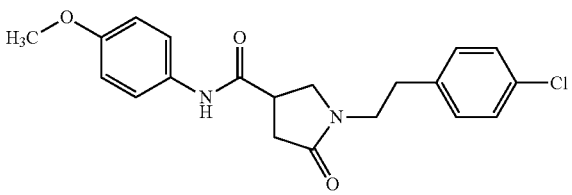

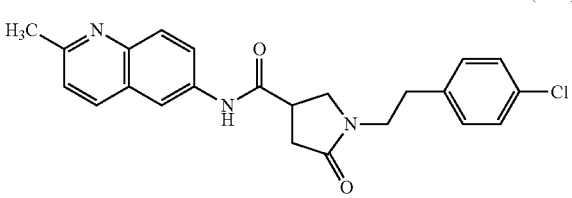

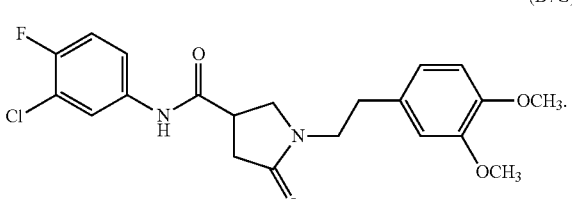

14. The pharmaceutical composition of claim 1, wherein the composition is adapted in a dosage form suitable for oral administration, the dosage form being a tablet capsule or lozenge.

15. The pharmaceutical composition of claim 14, wherein the composition is in the form of a tablet or capsule.

16. The pharmaceutical composition of claim 1, wherein the formulation is in a dosage form suitable for parenteral administration, wherein said parenteral administration is selected from the group consisting of intratumor, intravenous, subcutaneous, intraperitoneal, and intramuscular administration.

17. The pharmaceutical composition of claim 15, wherein the dosage form is a rolled or compressed tablet.

18. The pharmaceutical composition of claim 15, wherein the dosage form is a liquid formulation contained within a soft or hard capsule.

19. The pharmaceutical composition of claim 17, comprising one or more of:
   (a) a carrier comprising calcium phosphate, magnesium stearate, talc, sugars, lactose, dextrin, starch, gelatin, cellulose, methyl cellulose, sodium carboxymethyl cellulose, polyvinylpyrrolidine, or a combination thereof;
   (b) a disintegrant comprising sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch, sodium alginate, or a combination thereof;
   (c) a binder comprising microcrystalline cellulose, gelatin, sugar, polyethylene glycol, a natural or synthetic gum, polyvinylpyrrolidone, pregelatinized starch, hydroxypropyl cellulose, hydroxypropyl methylcellulose, or a combination thereof;
   (d) a diluent comprising lactose, mannitol, xylitol, dextrose, sucrose, sorbitol, microcrystalline cellulose, starch, dibasic calcium phosphate dehydrate, or a combination thereof;
   (e) a surface active agent comprising sodium lauryl sulfate, polysorbate 80, or a combination thereof;
   (f) a glidant comprising silicon dioxide, talc, or a combination thereof;
   (g) a lubricant comprising magnesium stearate, calcium stearate, zinc stearate, sodium stearyl fumarate, or a combination thereof;
   (h) a flavoring or taste-masking agent.

20. The pharmaceutical composition of claim 1, wherein the dosage form is suitable for topical administration.

21. The pharmaceutical composition of claim 20, wherein the dosage form is a gel, lotion, cream, ointment, or foam comprising an alcohol, water, mineral oil, liquid petrolatum, white petrolatum, glycerin, polyethylene glycol, or propylene glycol carrier.

22. The pharmaceutical composition of claim 1, wherein the dosage form is a suppository or pessary.

23. The pharmaceutical composition of claim 1, wherein the compound having a structure of Formula I is present in a therapeutically effective amount for treating Crohn's disease, inflammatory bowel disease, or colitis.

24. The composition of claim 17 wherein the pharmaceutically acceptable carrier is selected from the group consisting of calcium phosphate, magnesium stearate, talc, lactose, dextrin, starch, gelatin, cellulose, sodium carboxymethyl cellulose, and polyvinylpyrrolidine or a combination thereof.

25. The pharmaceutical composition of claim 17, wherein: (a) the carrier is selected from the group consisting of calcium phosphate, magnesium stearate, talc, lactose, dextrin, starch, gelatin, cellulose, sodium carboxymethyl cellulose, and polyvinylpyrrolidine, or a combination thereof: (b) the diluent is selected from the group consisting of lactose, mannitol, xylitol, dextrose, sucrose, sorbitol, microcrystalline cellulose, starch and dibasic calcium phosphate dihydrate, or a combination thereof: and (c) the excipient is selected from the group consisting of l-leucine, magnesium stearate, dextran, glucose, maltose, fructose, and trehalose.

* * * * *